(12) United States Patent
Burgi

(10) Patent No.: US 9,028,502 B2
(45) Date of Patent: May 12, 2015

(54) CERAMIC IMPLANT HOLDER

(71) Applicant: Greatbatch Medical S.A., Orvin (CH)

(72) Inventor: Jonas Burgi, Moutier (CH)

(73) Assignee: Greatbatch Medical S.A., Clarence, NY (US)

( * ) Notice: Subject to any disclaimer, the term of this patent is extended or adjusted under 35 U.S.C. 154(b) by 313 days.

(21) Appl. No.: 13/625,023

(22) Filed: Sep. 24, 2012

(65) Prior Publication Data

US 2013/0079785 A1    Mar. 28, 2013

Related U.S. Application Data

(60) Provisional application No. 61/538,313, filed on Sep. 23, 2011.

(51) Int. Cl.
| | | |
|---|---|---|
| *A61B 17/56* | (2006.01) | |
| *A61B 17/58* | (2006.01) | |
| *A61F 2/32* | (2006.01) | |
| *A61F 2/46* | (2006.01) | |
| *A61F 2/30* | (2006.01) | |

(52) U.S. Cl.
CPC ..... *A61F 2/4609* (2013.01); *A61F 2002/30205* (2013.01); *A61F 2002/30327* (2013.01);
(Continued)

(58) Field of Classification Search
CPC .... A61B 17/92; A61B 17/921; A61B 17/922; A61B 17/924; A61B 17/925; A61B 17/927; A61B 17/928; A61B 2017/922; A61B 2017/924; A61B 2017/925; A61B 2017/927; A61B 2017/928; A61F 2/4609; A61F 2/46; A61F 2/4603
USPC .......... 606/81, 86 A, 86 B, 86 R, 91, 99, 100; 623/22.11–22.39; 294/207
See application file for complete search history.

(56) References Cited

U.S. PATENT DOCUMENTS

| | | |
|---|---|---|
| 1,942,422 A | 6/1931 | Hanna |
| D272,648 S | 2/1984 | Bolesky et al. |
| D273,806 S | 5/1984 | Bolesky et al. |
| 4,475,549 A | 10/1984 | Oh |
| 4,520,511 A | 6/1985 | Gianezio et al. |

(Continued)

FOREIGN PATENT DOCUMENTS

| | | |
|---|---|---|
| EP | 0453694 | 10/1991 |
| EP | 0470912 | 12/1992 |

(Continued)

OTHER PUBLICATIONS

Smith & Nephew Polarcup Dual Mobility System, Dec. 2006.
(Continued)

*Primary Examiner* — Christian Sevilla
*Assistant Examiner* — Eric S Gibson
(74) *Attorney, Agent, or Firm* — Steven W. Winn; Michael F. Scalise

(57) ABSTRACT

An orthopedic prosthetic impactor used for the implantation of double mobility cup implants is described. The impactor consists of a drive train, a C-shaped housing, and a prosthetic cup engaging subassembly. The subassembly comprises an impaction plate, a primary cup contacting member, a secondary cup contacting member and a wedging assembly. The primary and secondary cup contacting members, contactable with an interior surface of the prosthetic cup implant. When activated by the drive train, the wedging assembly moves in a proximal direction towards the impaction plate, positioning the wedging assembly in a contactable relationship with the primary and secondary members thereby preventing the members and a connected prosthetic implant cup from moving during implantation.

38 Claims, 14 Drawing Sheets

(52) U.S. Cl.
CPC ............. *A61F 2002/30367* (2013.01); *A61F 2002/30387* (2013.01); *A61F 2002/30484* (2013.01); *A61F 2002/30505* (2013.01); *A61F 2002/30571* (2013.01); *A61F 2002/3208* (2013.01); *A61F 2002/4627* (2013.01); *A61F 2002/4681* (2013.01)

(56) References Cited

U.S. PATENT DOCUMENTS

| | | | |
|---|---|---|---|
| 4,528,980 A | 7/1985 | Kenna | |
| 4,587,964 A | 5/1986 | Walker et al. | |
| 4,632,111 A | 12/1986 | Roche | |
| 4,716,894 A | 1/1988 | Lazzeri et al. | |
| 4,765,328 A | 8/1988 | Keller et al. | |
| 4,904,267 A | 2/1990 | Bruce et al. | |
| 4,919,679 A | 4/1990 | Averill et al. | |
| 4,921,493 A | 5/1990 | Webb, Jr. et al. | |
| 5,019,105 A | 5/1991 | Wiley | |
| 5,037,424 A | 8/1991 | Aboczky | |
| 5,059,196 A * | 10/1991 | Coates | 606/99 |
| 5,061,270 A | 10/1991 | Aboczky | |
| 5,062,854 A | 11/1991 | Noble et al. | |
| 5,089,003 A | 2/1992 | Fallin et al. | |
| 5,116,339 A | 5/1992 | Glock | |
| 5,124,106 A | 6/1992 | Morr et al. | |
| 5,133,766 A | 7/1992 | Halpern | |
| 5,169,399 A | 12/1992 | Ryland et al. | |
| 5,171,313 A * | 12/1992 | Salyer | 606/86 R |
| 5,190,549 A | 3/1993 | Miller et al. | |
| 5,234,432 A | 8/1993 | Brown | |
| 5,261,915 A | 11/1993 | Durlacher et al. | |
| 5,324,293 A | 6/1994 | Rehmann | |
| 5,342,362 A | 8/1994 | Kenyon et al. | |
| 5,364,403 A | 11/1994 | Petersen et al. | |
| 5,417,696 A | 5/1995 | Kashuba et al. | |
| 5,443,471 A | 8/1995 | Swajger | |
| 5,454,815 A | 10/1995 | Geisser et al. | |
| 5,485,887 A | 1/1996 | Mandanis | |
| 5,540,697 A * | 7/1996 | Rehmann et al. | 606/91 |
| 5,658,294 A | 8/1997 | Sederholm | |
| 5,665,091 A | 9/1997 | Noble et al. | |
| 5,683,399 A | 11/1997 | Jones | |
| 5,707,374 A | 1/1998 | Schmidt | |
| 5,762,391 A * | 6/1998 | Sumnitsch | 294/119.1 |
| 5,863,295 A | 1/1999 | Averill et al. | |
| 5,913,860 A | 6/1999 | Scholl | |
| 5,928,287 A * | 7/1999 | Keller | 623/22.21 |
| 5,931,518 A * | 8/1999 | Pirker | 294/119.1 |
| 5,954,727 A * | 9/1999 | Collazo | 606/91 |
| 5,976,148 A | 11/1999 | Charpenet et al. | |
| 5,993,455 A | 11/1999 | Noble | |
| 6,063,124 A | 5/2000 | Amstutz | |
| 6,120,508 A | 9/2000 | Grunig et al. | |
| 6,197,065 B1 | 3/2001 | Martin et al. | |
| 6,432,141 B1 | 8/2002 | Stocks et al. | |
| 6,451,058 B2 | 9/2002 | Tuke et al. | |
| 6,626,913 B1 | 9/2003 | McKinnon et al. | |
| 6,663,636 B1 | 12/2003 | Lin | |
| 6,811,569 B1 | 11/2004 | Afriat et al. | |
| 6,827,381 B1 * | 12/2004 | Reichert et al. | 294/207 |
| 7,192,449 B1 | 3/2007 | McQueen et al. | |
| 7,335,207 B1 | 2/2008 | Smith | |
| 7,341,593 B2 | 3/2008 | Auxepaules et al. | |
| 7,396,357 B2 | 7/2008 | Tornier et al. | |
| 7,585,301 B2 | 9/2009 | Santarella et al. | |
| 7,591,821 B2 | 9/2009 | Kelman | |
| 7,604,667 B2 | 10/2009 | DeSmet et al. | |
| 7,621,921 B2 * | 11/2009 | Parker | 606/91 |
| 7,727,282 B2 * | 6/2010 | Slone et al. | 623/22.12 |
| 7,785,331 B2 * | 8/2010 | Leisinger et al. | 606/99 |
| 7,922,726 B2 | 4/2011 | White | |
| 8,021,370 B2 * | 9/2011 | Fenton et al. | 606/91 |
| 8,142,439 B2 * | 3/2012 | Parker | 606/91 |
| 8,236,003 B2 * | 8/2012 | Burgi | 606/91 |
| 8,277,457 B1 * | 10/2012 | Burgi et al. | 606/91 |
| 8,398,650 B1 * | 3/2013 | Burgi | 606/99 |
| 8,475,465 B2 * | 7/2013 | Teeny et al. | 606/99 |
| 2001/0051830 A1 | 12/2001 | Tuke et al. | |
| 2002/0004660 A1 | 1/2002 | Henniges et al. | |
| 2002/0116007 A1 | 8/2002 | Lewis | |
| 2002/0177854 A1 | 11/2002 | Tuke et al. | |
| 2002/0193797 A1 | 12/2002 | Johnson et al. | |
| 2003/0009234 A1 | 1/2003 | Treacy et al. | |
| 2003/0050645 A1 | 3/2003 | Parker et al. | |
| 2003/0083668 A1 | 5/2003 | Rogers et al. | |
| 2003/0088316 A1 | 5/2003 | Ganjianpour | |
| 2003/0187512 A1 | 10/2003 | Frederick et al. | |
| 2003/0220698 A1 | 11/2003 | Mears et al. | |
| 2003/0229356 A1 | 12/2003 | Dye | |
| 2004/0215200 A1 | 10/2004 | Tornier et al. | |
| 2005/0038443 A1 | 2/2005 | Hedley et al. | |
| 2005/0075736 A1 | 4/2005 | Collazo | |
| 2005/0137603 A1 | 6/2005 | Belew et al. | |
| 2005/0171548 A1 | 8/2005 | Kelman | |
| 2005/0187562 A1 | 8/2005 | Grimm et al. | |
| 2005/0222572 A1 | 10/2005 | Chana | |
| 2005/0228395 A1 | 10/2005 | Auxepaules et al. | |
| 2005/0234462 A1 | 10/2005 | Hershberger | |
| 2005/0246031 A1 | 11/2005 | Frederick et al. | |
| 2006/0052780 A1 | 3/2006 | Errico et al. | |
| 2006/0149285 A1 | 7/2006 | Burgi et al. | |
| 2006/0241781 A1 * | 10/2006 | Brown et al. | 623/23.43 |
| 2007/0010825 A1 * | 1/2007 | Leisinger et al. | 606/99 |
| 2007/0156155 A1 | 7/2007 | Parker | |
| 2007/0167952 A1 | 7/2007 | Burgi et al. | |
| 2007/0225725 A1 | 9/2007 | Heavener et al. | |
| 2007/0270783 A1 | 11/2007 | Zumsteg et al. | |
| 2007/0288096 A1 | 12/2007 | Surma | |
| 2007/0293869 A1 | 12/2007 | Conte et al. | |
| 2008/0004628 A1 | 1/2008 | White | |
| 2008/0021481 A1 | 1/2008 | Burgi | |
| 2008/0033444 A1 | 2/2008 | Bastian et al. | |
| 2008/0077229 A1 * | 3/2008 | Gradel | 623/22.15 |
| 2008/0146969 A1 | 6/2008 | Kurtz | |
| 2008/0154261 A1 * | 6/2008 | Burgi | 606/53 |
| 2008/0243127 A1 | 10/2008 | Lang et al. | |
| 2008/0255455 A1 | 10/2008 | Fletcher | |
| 2008/0255568 A1 | 10/2008 | Tornier et al. | |
| 2008/0262503 A1 | 10/2008 | Muller | |
| 2009/0112214 A1 | 4/2009 | Philippon et al. | |
| 2009/0182334 A1 | 7/2009 | Brehm | |
| 2009/0192515 A1 | 7/2009 | Lechot et al. | |
| 2009/0240256 A1 | 9/2009 | Smith | |
| 2009/0281545 A1 | 11/2009 | Stubbs | |
| 2012/0053592 A1 * | 3/2012 | Burgi | 606/91 |
| 2012/0136361 A1 * | 5/2012 | Aux Epaules et al. | 606/91 |
| 2013/0079785 A1 * | 3/2013 | Burgi | 606/91 |

FOREIGN PATENT DOCUMENTS

| | | |
|---|---|---|
| EP | 0535973 | 4/1993 |
| EP | 3 7302 | 7/1994 |
| EP | 638299 | 12/1995 |
| EP | 1308140 | 5/2003 |
| EP | 119 687 | 7/2004 |
| EP | 1438936 | 7/2004 |
| EP | 1447058 | 8/2004 |
| WO | 9511641 | 5/1995 |
| WO | 0012832 | 3/2000 |
| WO | 2005044153 | 5/2005 |
| WO | 2006061708 | 6/2006 |
| WO | 2007098549 | 9/2007 |
| WO | 2008128282 | 10/2008 |
| WO | 2009136284 | 11/2009 |

OTHER PUBLICATIONS

European Search Report dated Apr. 15, 2011.
Duraloc Option, Ceramic Acetabular Cup System, DePuy, Sep. 18, 2006.

* cited by examiner

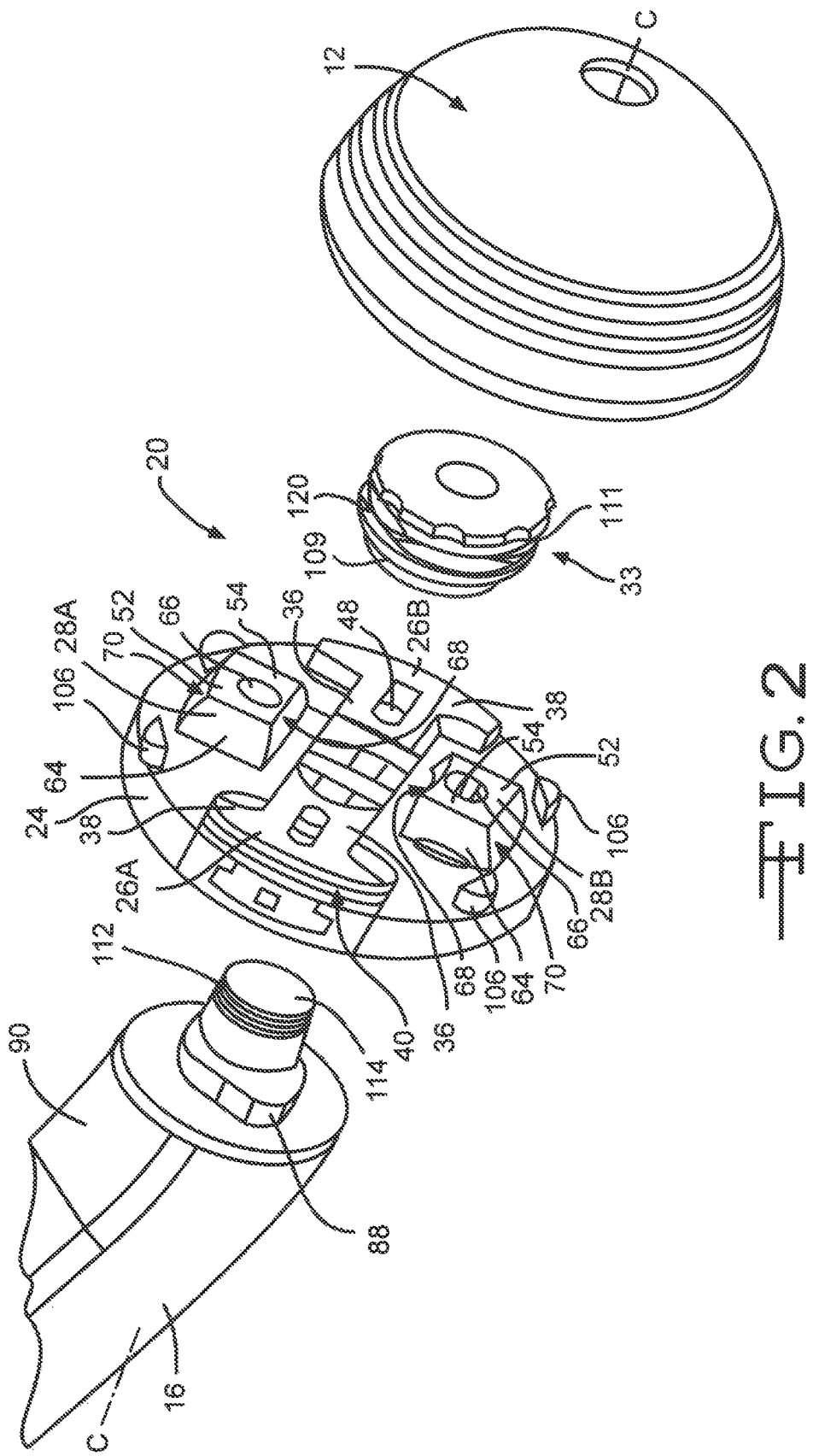

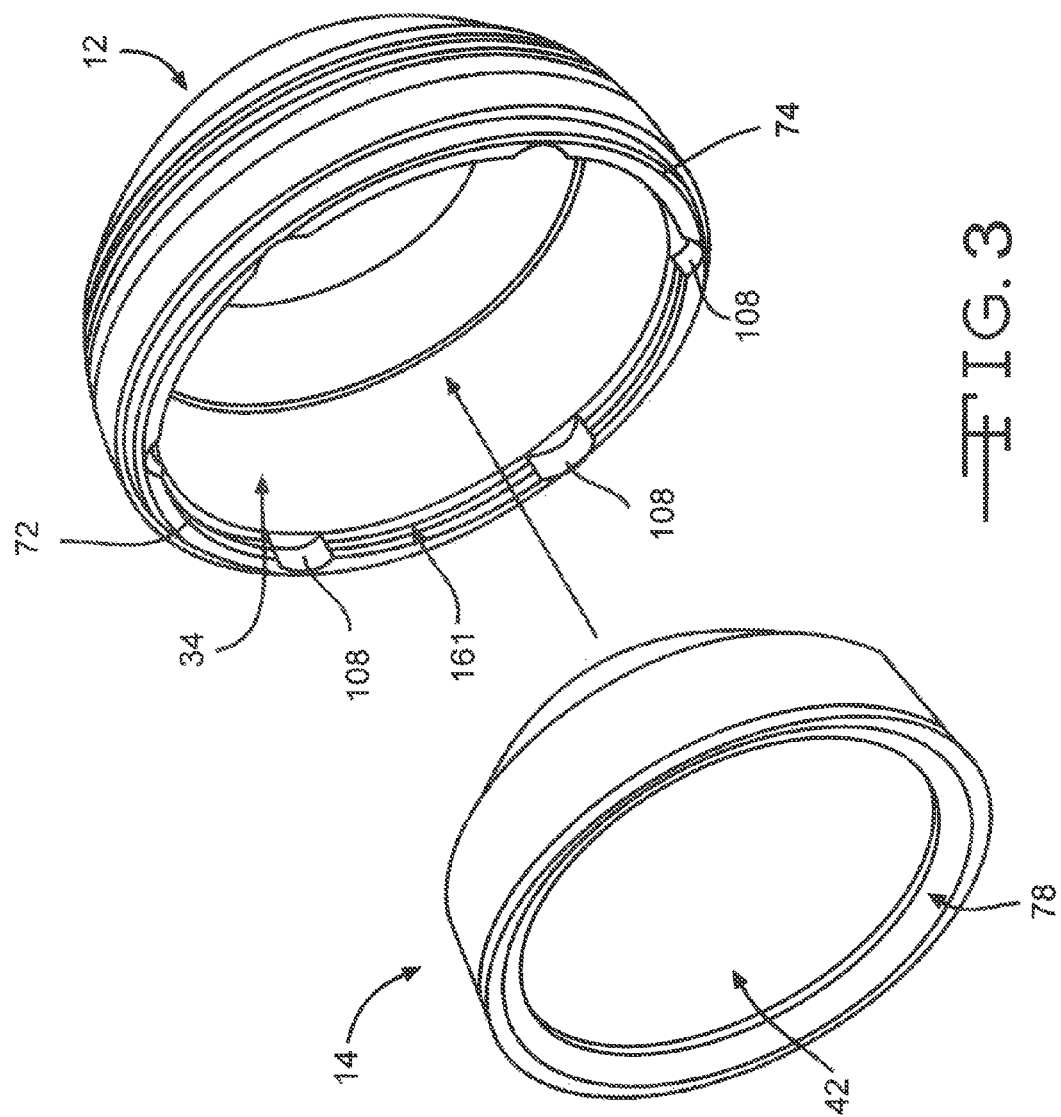

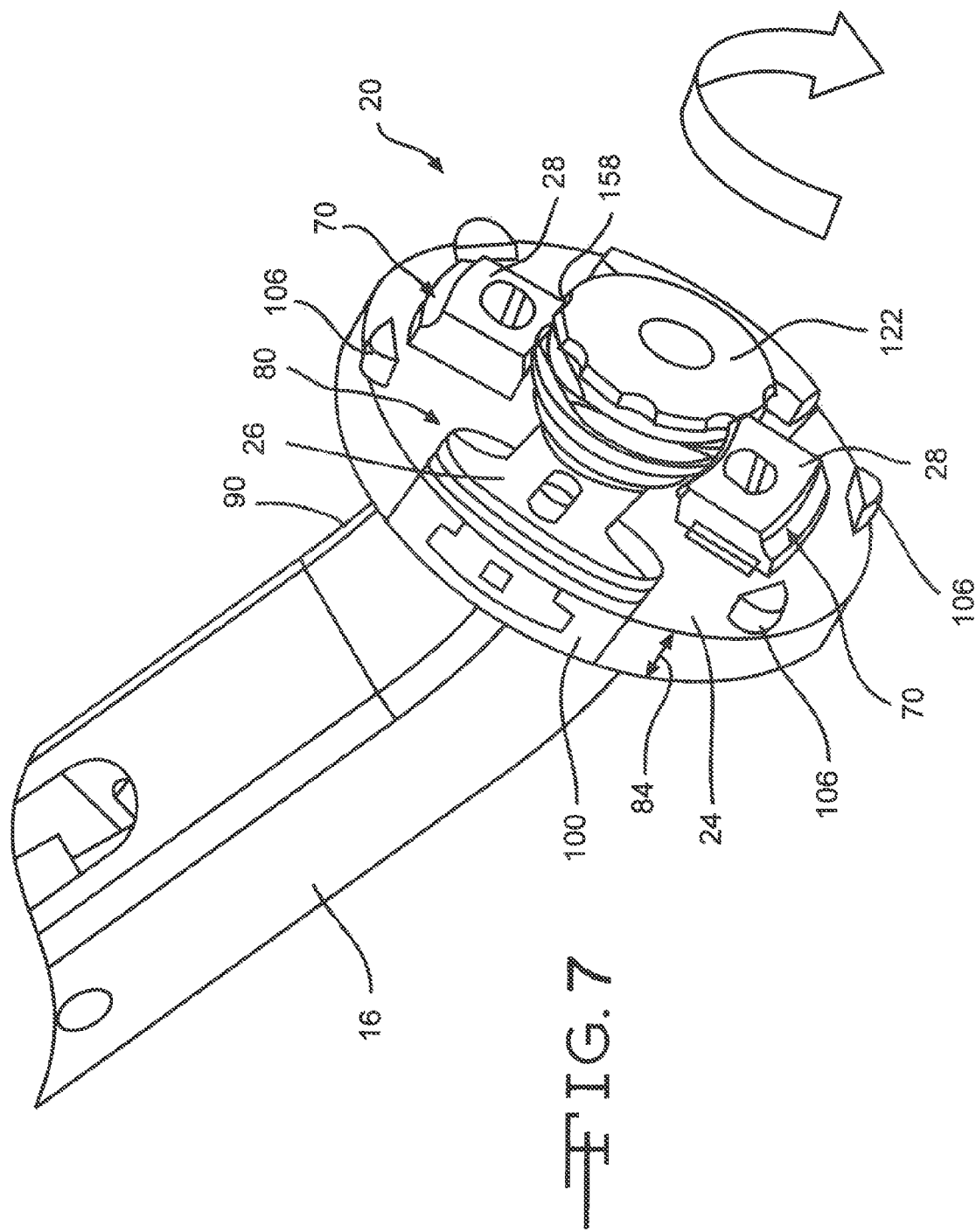

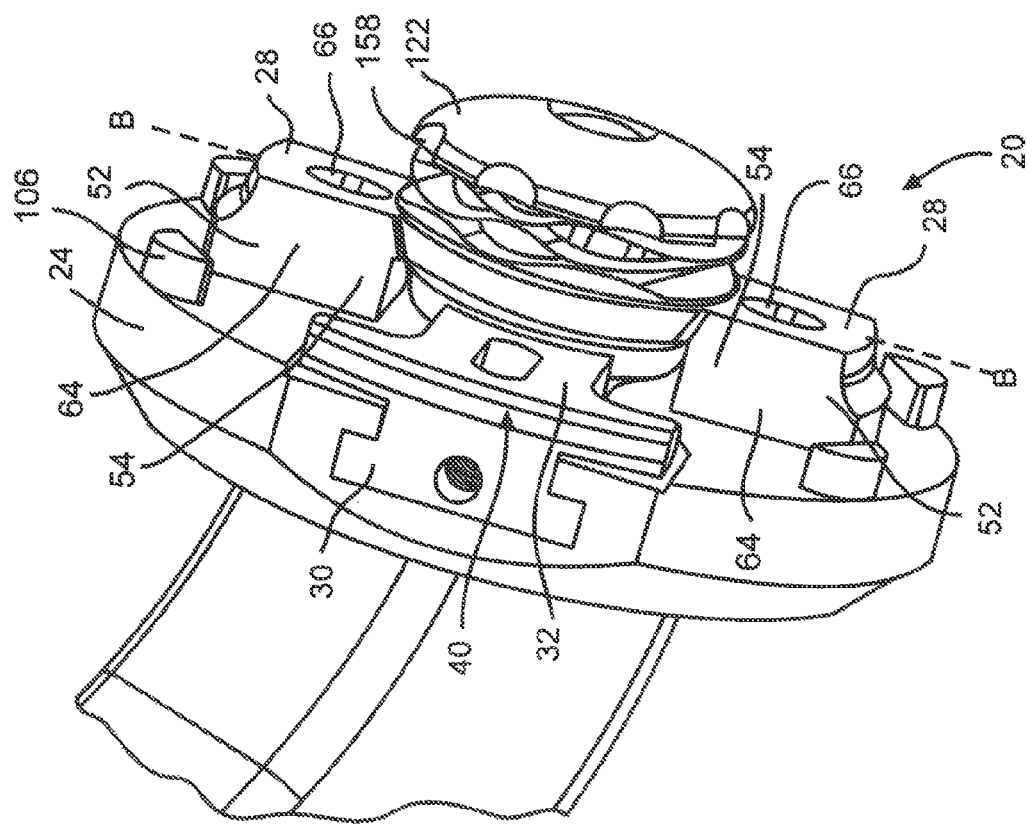
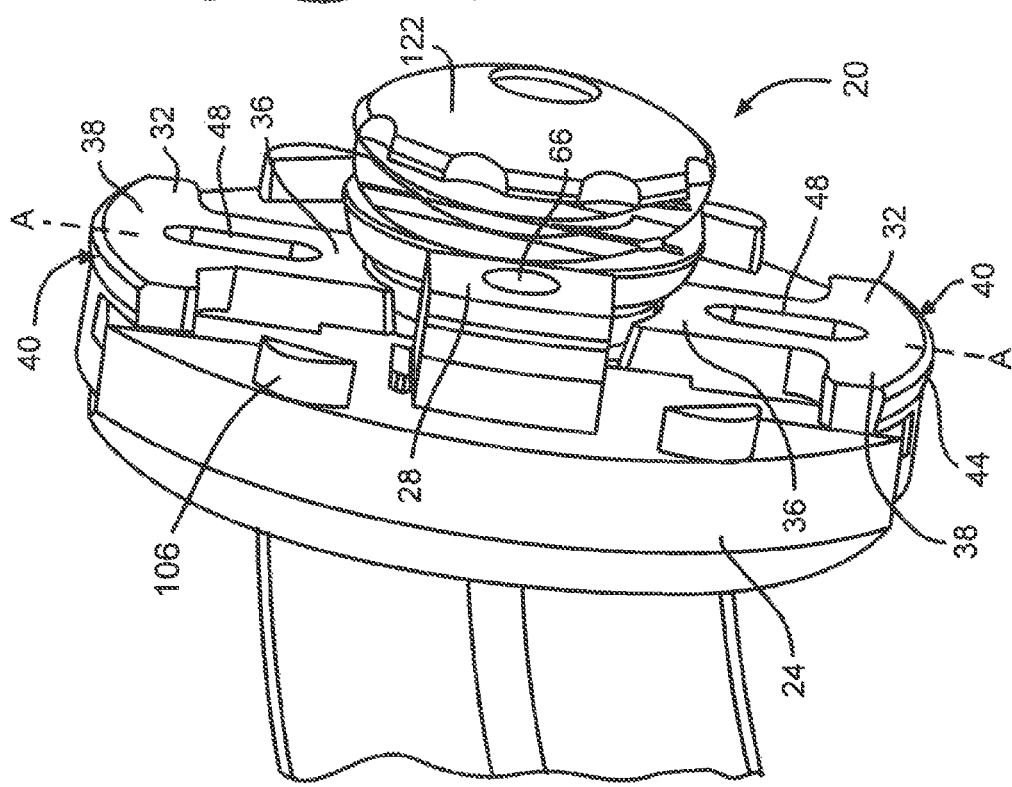

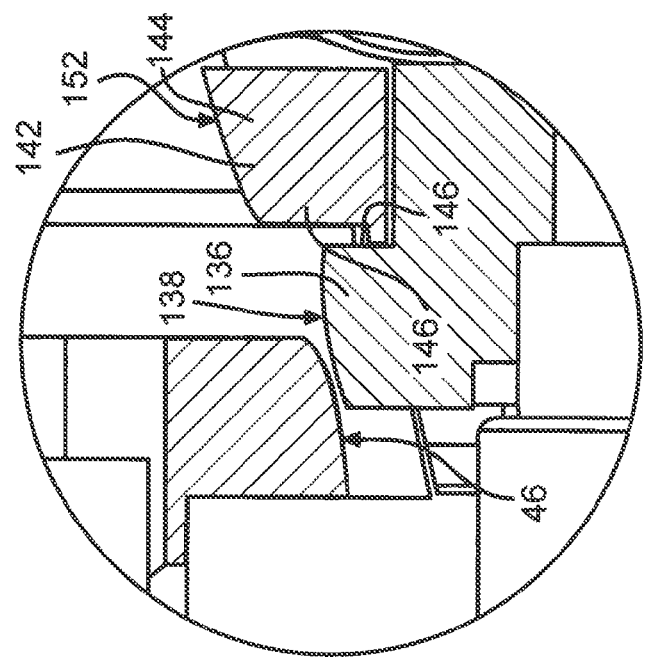
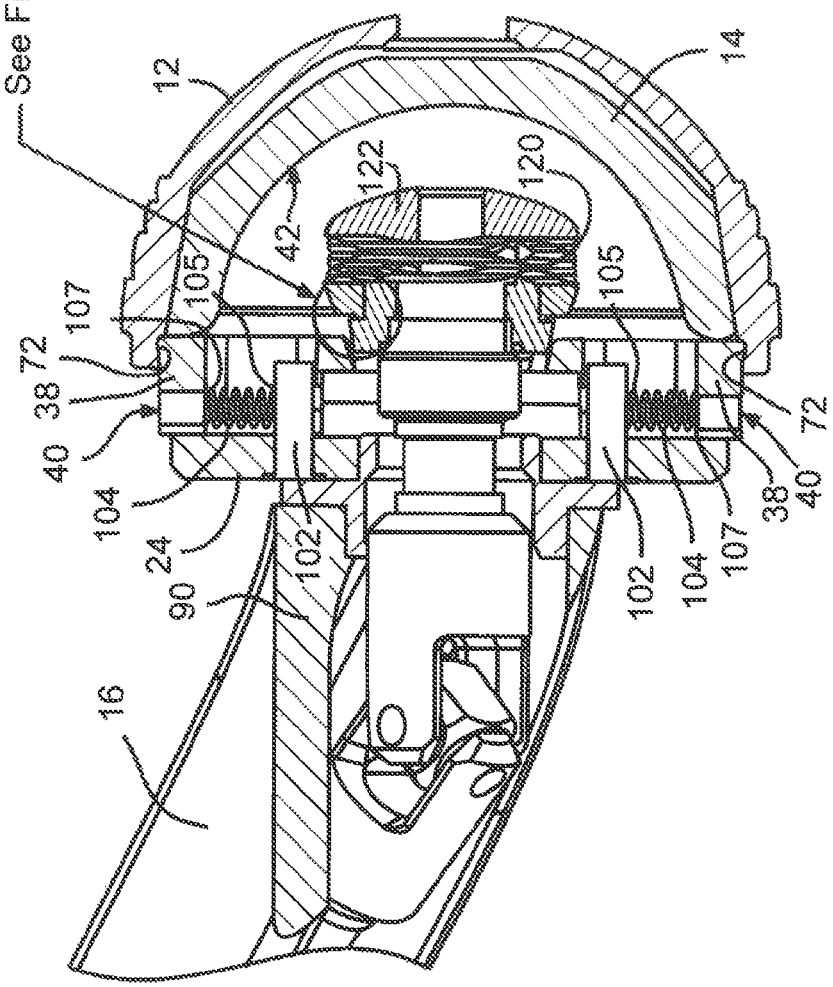

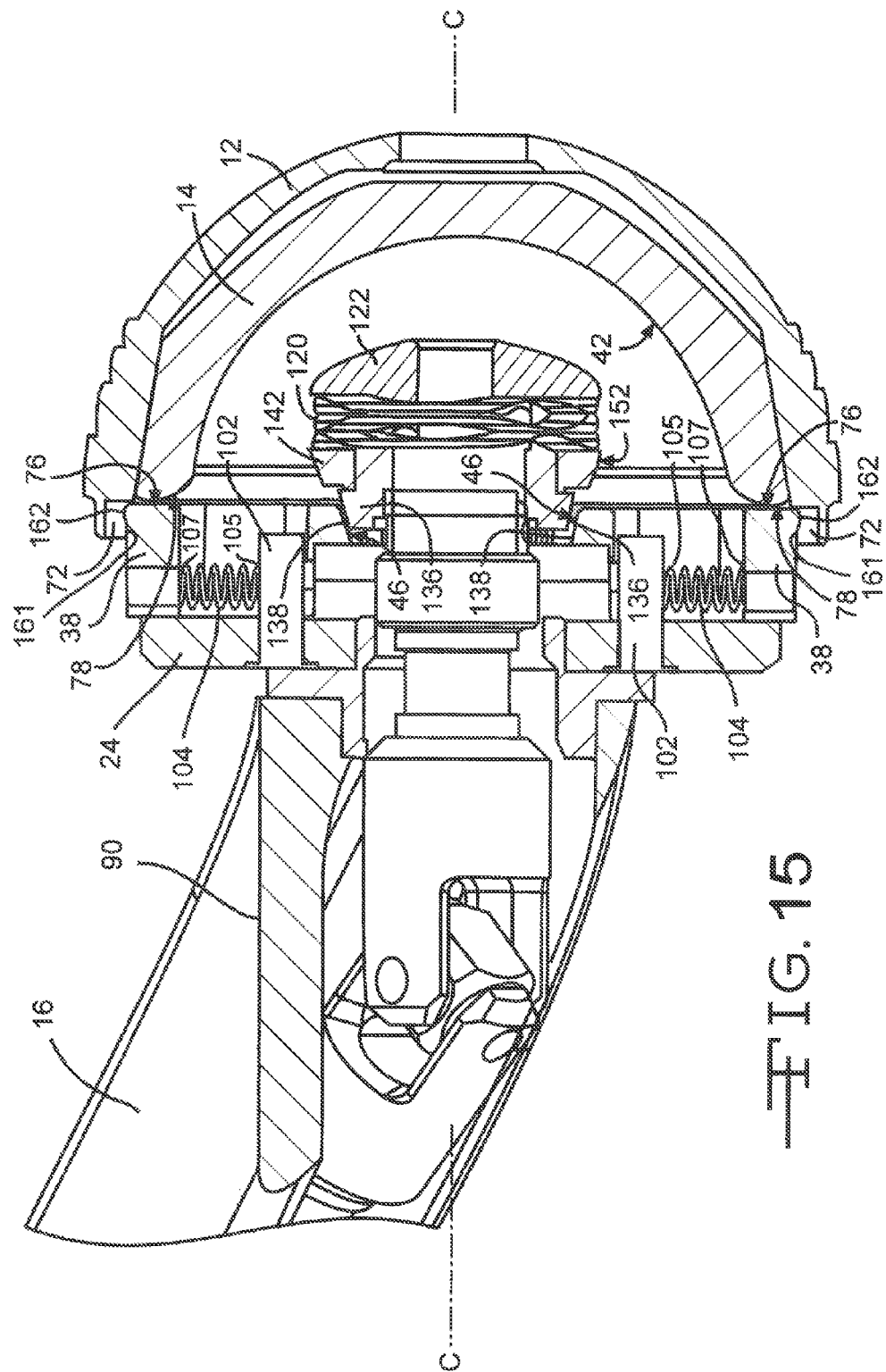

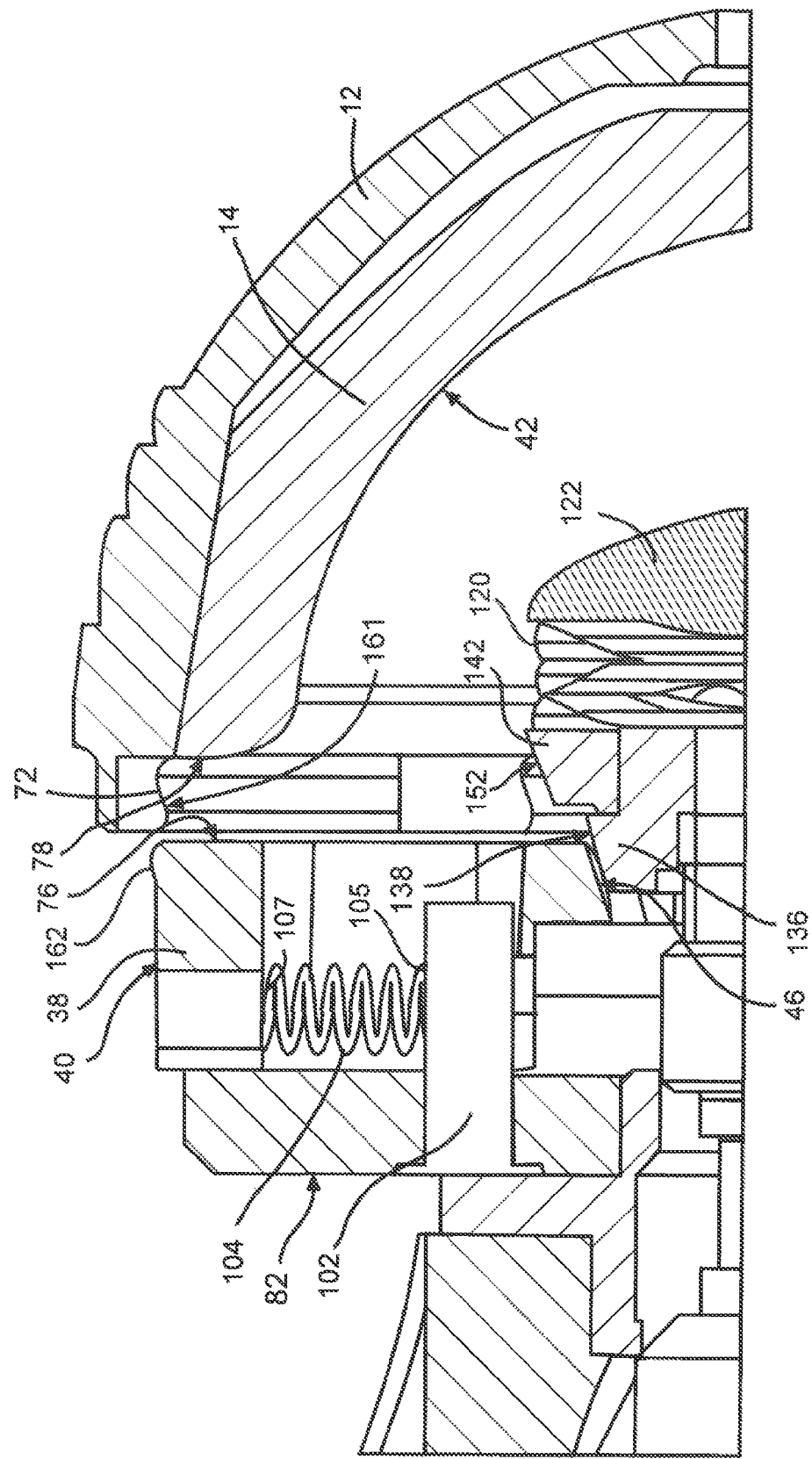

CERAMIC IMPLANT HOLDER

CROSS-REFERENCE TO RELATED APPLICATION

This application claims priority to U.S. provisional application Ser. No. 61/538,313, filed on Sep. 23, 2011.

FIELD OF THE INVENTION

This invention relates to surgical impactors for aiding in installing orthopedic prostheses, and more specifically, to an improved grasping mechanism for installing acetabular implants in the acetabular socket.

BACKGROUND OF THE INVENTION

A double mobility prosthetic cup is a type of acetabular implant that is designed to increase a patient's range of hip mobility. Unlike other types of acetabular implants, double mobility prosthetic cups do not have an opening through the cup portion which allows for easy manipulation during implantation. For example, a rod is typically threaded through the cup opening to the apex of the cup dome where there is typically a threaded hole. This rod is used like a handle with which to control and guide the implant during implantation. Double mobility implants, on the other hand, do not have such an opening and therefore create a challenge in controlling them during implantation. The present invention solves this problem and provides an effective novel means of manipulating the double mobility implant during implantation.

Complicated mechanical devices have crevices and recesses that are difficult, if not almost impossible to clean with ease. Devices that are not properly cleaned and sterilized run the risk of disease transfer from patient to patient following the emergence of certain "prions" that are not killed by normal hospital sterilization and need to be physically removed by washing and rinsing.

During implantation of the prosthetic cup, a great amount of mechanical force is delivered to the cup implant. Generally, an impacting force is delivered to the proximal end of the impactor which is then imparted to the prosthetic cup at the distal end. The application of such mechanical impacting forces could damage the implant cup, particularly a double mobility prosthetic cup implant since these types of cup implants generally lack the mechanical strength to withstand the application of impaction forces throughout the prosthetic cup. Furthermore, these double mobility prosthetic cups are precisely machined with smooth surfaces. As such, the machined surfaces of these implants could become structurally deformed, cracked or scratched during implantation. In addition, many double mobility prosthetic cups may comprise an insert liner, commonly made of a ceramic material, that is positioned along the interior surface within the cavity of the prosthetic cup. These inserts provide a protective barrier that allows for smooth movement between a metallic joint and the metallic prosthetic cup. Like the prosthesis cup, these inserts could also become structurally deformed, cracked or scratched during implantation. Such damage to the cup and/or cup insert could result in a decrease of mobility for the patient or the need to repeat the prosthetic cup implantation process. Damage could also increase the risk of higher wear rates for the bearing components leading to possible earlier device failure.

Further, in surgical procedures in which access to the treatment site is limited, it is difficult to use current impactors without subjecting the patient to repeated abrasion and tissue trauma when inserting, operating and extracting surgical instruments.

Still further, once the appropriate position of the implant is selected, it is often difficult to ensure that the position does not change upon insertion of the assembly through the incision.

What is needed, therefore, is a double mobility implant impactor that minimizes the potential of damaging the cup implant during implantation. Further, the present invention provides an impactor that is easily adjustable, operatable, disassemblable, and cleanable. Still further, what is needed is an impactor that enables the surgeon to better maneuver, position and install the double mobility implant in a particular angular orientation.

SUMMARY OF THE INVENTION

The present invention relates to an acetabular impactor that aids a surgeon in controlling the installation of a double mobility acetabular prosthesis cup. The impactor has a housing which encloses a drive train having, at a far end, a double mobility prosthetic engaging subassembly, and at the opposite end, a handle which facilitates activation of the drive train and movement of the subassembly. The impactor enables easy orientation of a double mobility prosthesis attached to its end. This is important because precise control of the prosthetic is critical in implantation of the prosthetic in a patient.

The subassembly comprises a series of components, an impaction plate having a plurality of cup contacting members positioned on an exterior surface of the plate and a wedging assembly attached to a drive rod. The wedging assembly further comprises a first conical body positioned adjacent a second conical body, a conical bias member and an end cap member. The wedging assembly is designed to lock the cup contacting members in direct contact with the prosthesis cup at differing depths within the cup's interior surface, thereby providing a secure fit therebetween. Once positioned within the body, the wedging assembly can be released and the impactor removed, thus leaving the prosthetic cup positioned within the body.

An objective of the invention is to provide a novel design by which the double mobility cup prosthesis is manipulated and inserted into the body with minimum stresses imparted to the cup. The present invention provides an impactor by which potential damage to the cup during the implantation procedure is minimized.

A further objective is to provide an impactor that can be "easily cleaned". Quick and modular disassembly of the impactor enables access to all surfaces that should be cleaned. The reduction in the number of small radius internal corners, crevices and small gaps and the absence of blind holes also aids in sterilization of the instrument.

BRIEF DESCRIPTION OF THE DRAWINGS

FIG. 2 shows a magnified perspective view of an embodiment of the components that comprise the prosthesis engaging subassembly.

FIG. 3 shows a perspective view of an embodiment of a prosthesis cup implant and a prosthesis cup insert.

FIGS. 6-7 illustrate perspective views of an embodiment of the prosthesis engaging subassembly being attached to the distal end of the housing.

FIGS. 8-9 illustrate perspective views of an embodiment of the prosthesis engaging subassembly attached to the distal end of the housing along imaginary axes A-A and B-B.

FIG. 13 shows a cross-sectional view of an embodiment of a prosthesis cup being connected to the prosthesis engaging subassembly, the wedging assembly having been moved in a further proximal direction.

FIG. 14 illustrates a magnified cross-sectional view of an embodiment of the position of the first and second bands of the first and second conical bodies with respect to the proximal end surfaces of the primary and secondary cup contacting members shown in FIG. 13.

FIG. 15 shows a magnified cross-sectional view of an embodiment of a prosthesis cup connected to the prosthesis engaging subassembly, the wedging assembly having been moved in a furthest proximal direction.

FIG. 16 illustrates a magnified cross-sectional view of an embodiment of the position of the first and second bands of the first and second conical bodies with respect to the proximal end surfaces of the primary and secondary cup contacting members shown in FIG. 15.

DETAILED DESCRIPTION OF THE PREFERRED EMBODIMENT(S)

Figure 1:
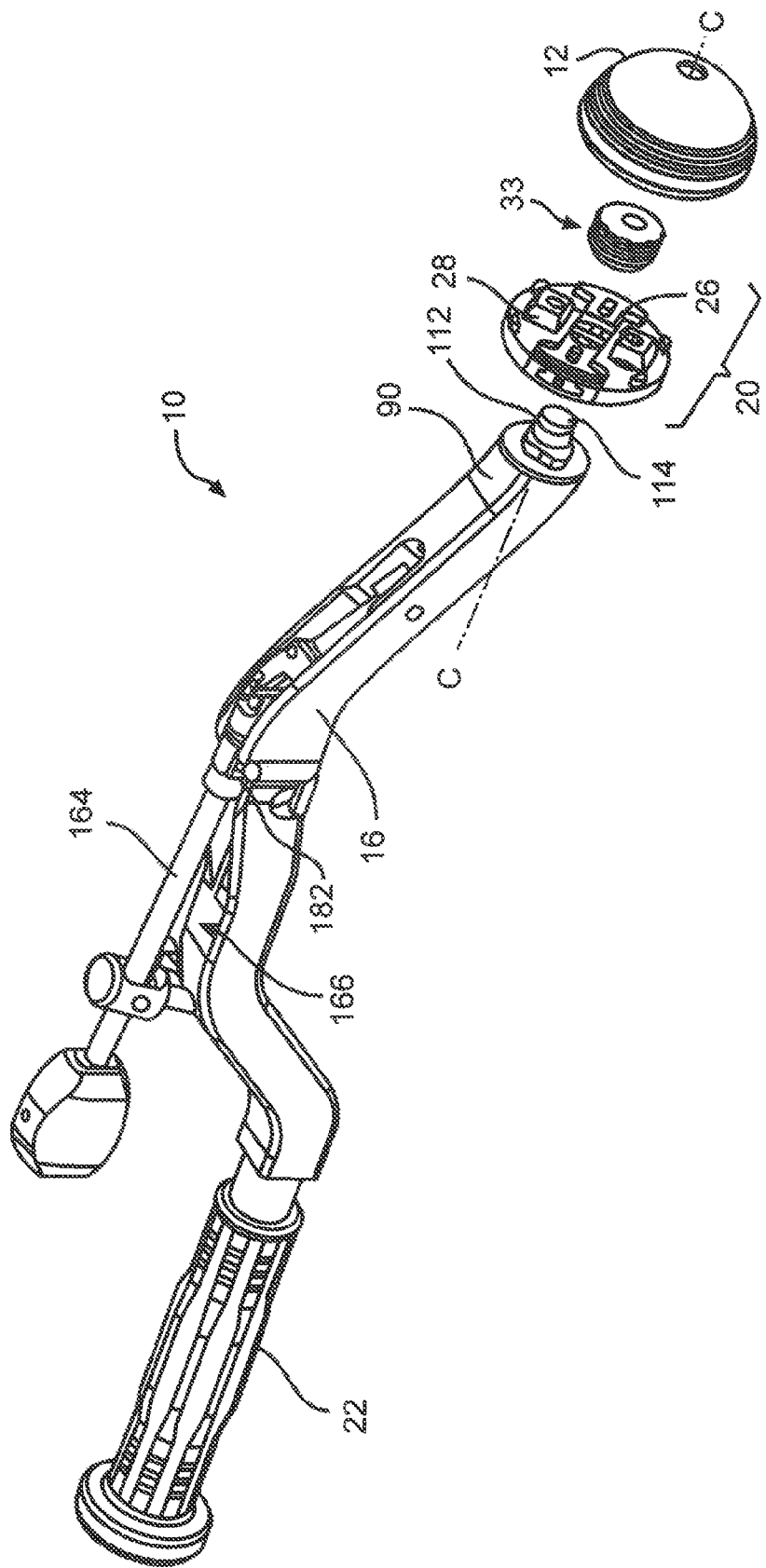
FIG. 1 is a perspective view of the impactor of the present invention.
Figure 1A:
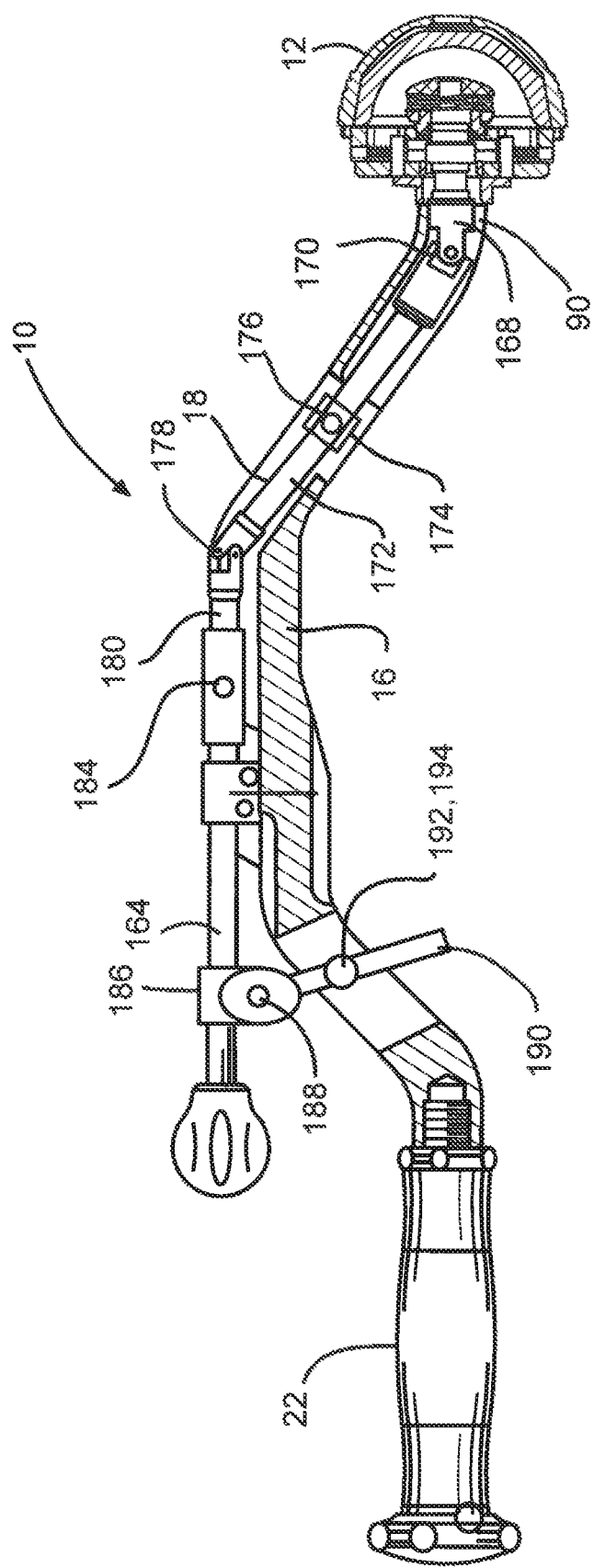
FIG. 1A is a cross-sectional side view of the impactor shown in FIG. 1.

Referring now to FIGS. 1-16, an acetabular impactor 10 is provided to aid the surgeon in controlling installation of an acetabular cup prosthesis 12 (FIG. 3) which may comprise a cup insert 14 positioned therewithin. The impactor 10 has a housing 16 which encloses a drive train 18 having, at a distal end, a prosthesis cup engaging subassembly 20, and at the proximal end, a handle 22 which facilitates moving of the drive train 18 by the operator. The housing 16 may be C-shaped, as shown, in order to minimize invasiveness of the surgery by better clearing anatomical structures and tissue.

The prosthesis cup engaging subassembly 20, as illustrated in FIGS. 1-2, 4, 6-11, 13 and 15, comprises an impaction plate 24, a primary cup contacting member 26, a secondary cup contacting member 28, and a wedging assembly 33. In a preferred embodiment, the prosthesis cup engaging subassembly 20 may comprise a plurality of primary and secondary cup contacting members 26, 28. As shown in FIGS. 1, 2, 4, 6-9, two primary cup contacting members 26 and two secondary cup contacting members 28 are illustrated. The two primary cup contacting members 26 are preferably positioned in an opposing orientation on the surface of the plate 24. Furthermore, the two secondary cup contacting members 28 are also positioned in an opposing orientation on the surface of the plate 24. As shown, first and second primary cup contacting members 26A, 26B are preferably positioned about 90.degree. from respective first and second secondary cup contacting members 28A, 28B (FIG. 2).

Figure 4:
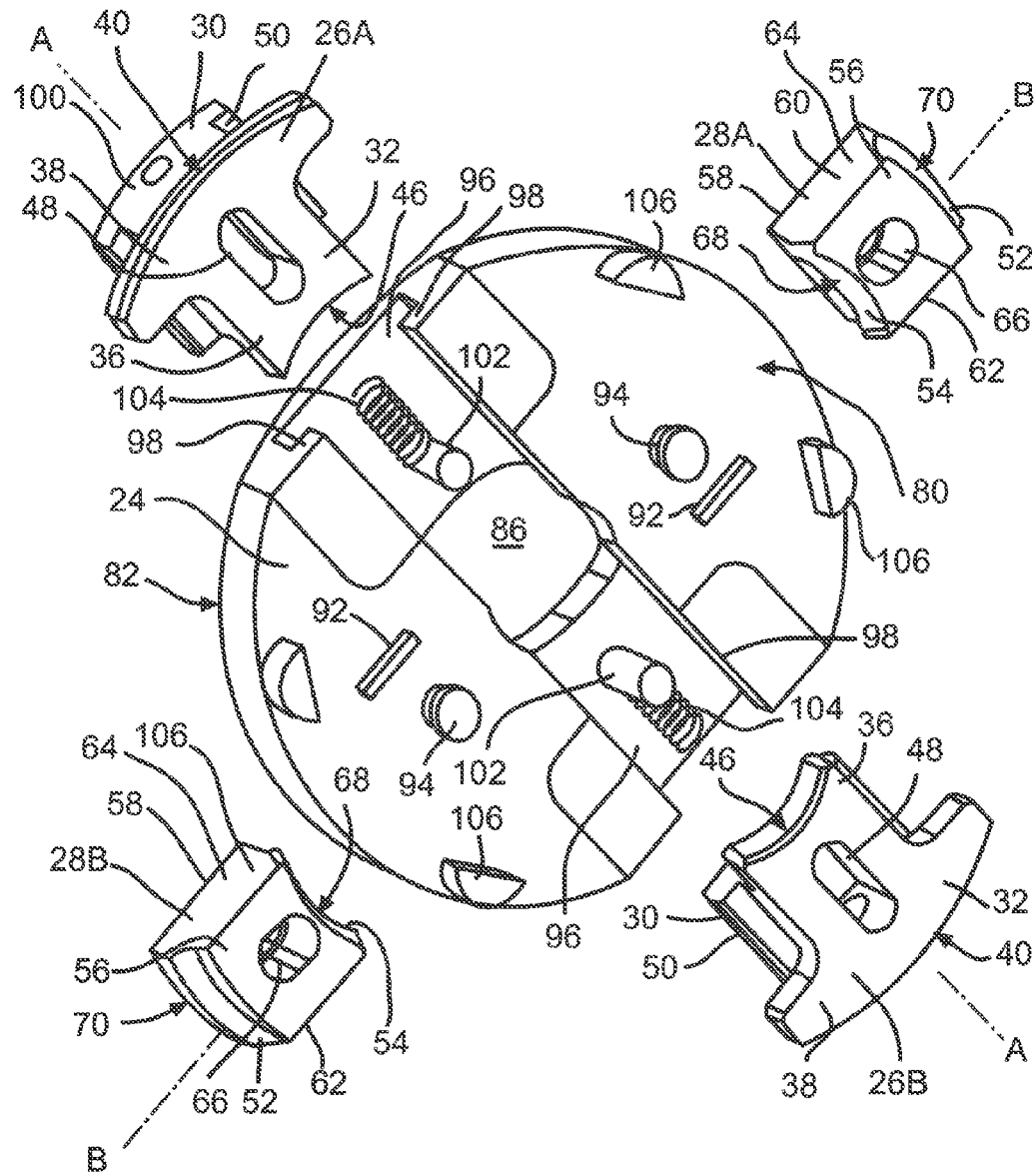
FIG. 4 illustrates a perspective view of an embodiment of the impaction plate and the primary and secondary cup contacting members of the prosthesis engaging subassembly.

As shown in FIG. 4, the primary cup contacting members 26A, 26B are positioned along imaginary axis A-A and the secondary cup contacting members 28A, 28B are positioned along imaginary axis B-B. Both imaginary axes, A-A and B-B, extend about parallel to the surface of the impaction plate 24 and are about perpendicular to each other.

As shown in FIGS. 2, 4, 6-7, the primary cup contacting member 26 comprises a lower primary cup contacting member body portion 30 that extends from an upper primary cup contacting member body portion 32. The upper body portion 32 is designed to contact an inner surface 34 of the prosthetic cup 12 and/or the cup insert 14 while the lower body portion 30 is designed to provide a means of attachment of the primary member 26 to the impaction plate 24. More specifically, the upper body portion 32 comprises a proximal end portion 36 spaced from a distal end portion 38 by an upper body portion length therebetween. In a preferred embodiment, the distal end portion. 38 of the upper body portion 32 of the primary cup contacting member 26 has an outwardly curved distal end surface 40. In a preferred embodiment, the distal end surface 40 is a convex surface that corresponds with an interior concave surface 34 of the prosthetic cup implant 12 or an interior surface 42 of the cup insert 14.

Figure 6:
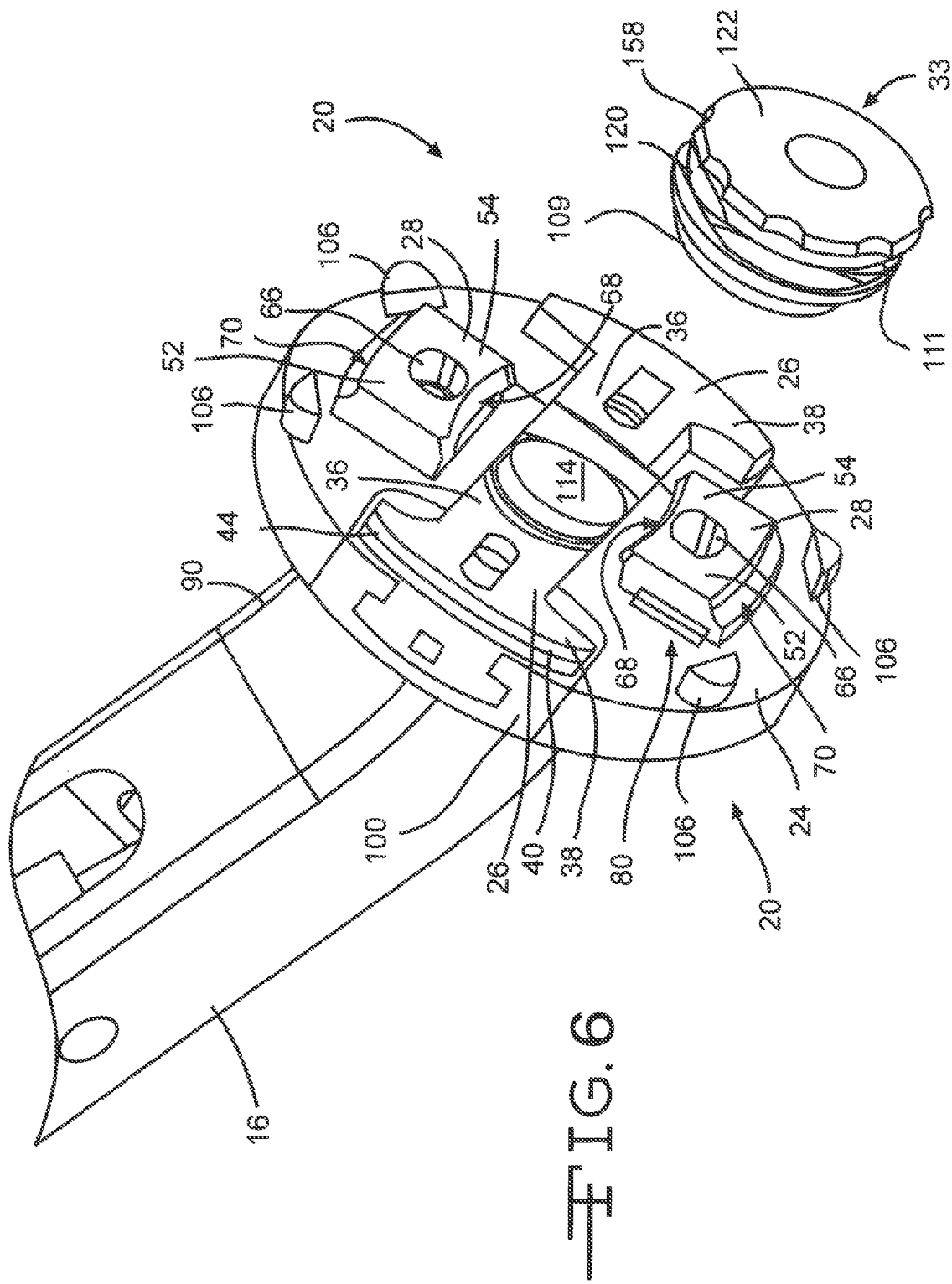
Figure 10:
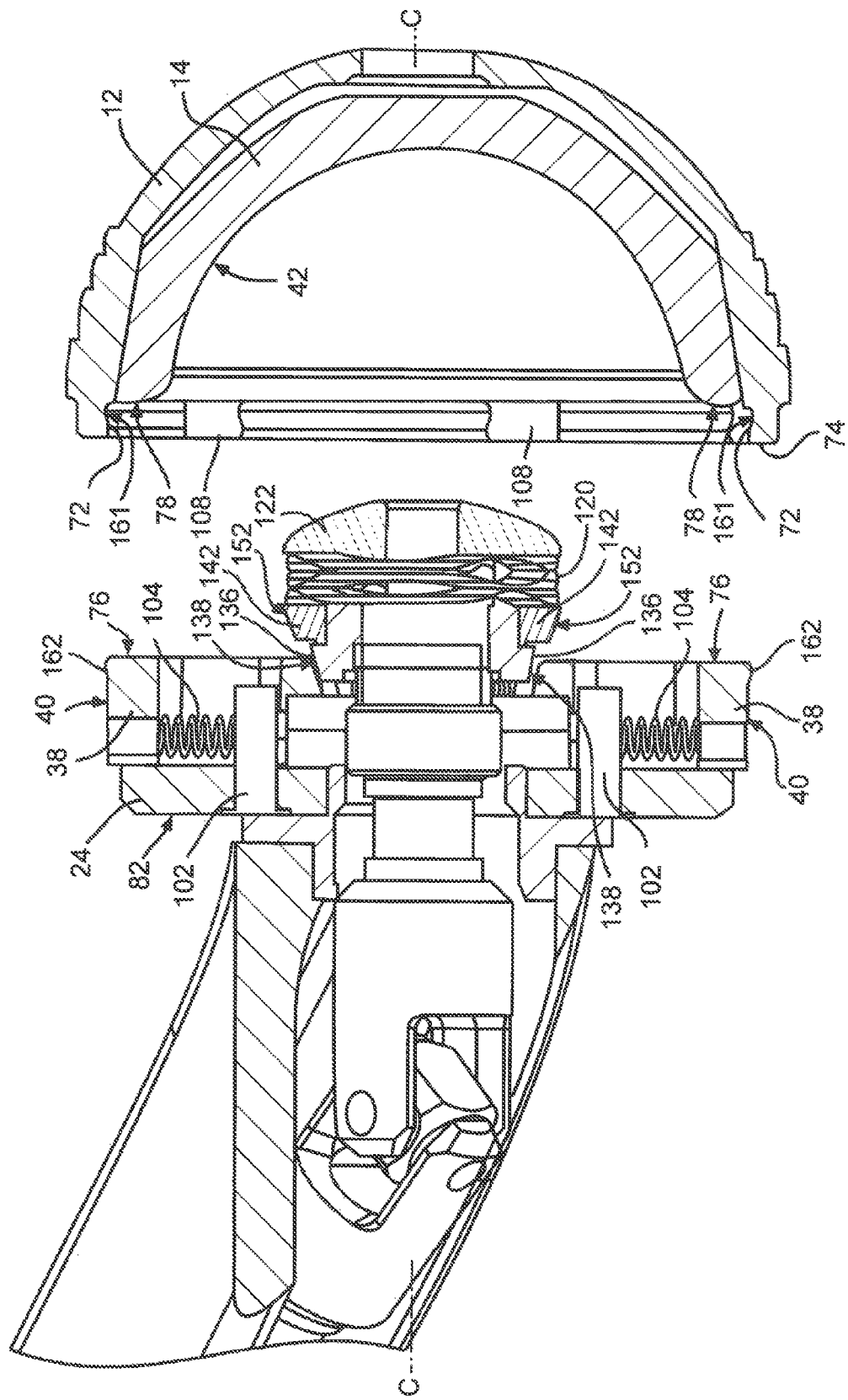
FIG. 10 illustrates a cross-sectional view of an embodiment of a prosthesis cup implant and cup insert ready to be attached to the prosthesis engaging subassembly.

As shown in FIG. 6, the distal end surface 40 may have a protruding distal end ridge portion 44. This ridge 44 is designed to contact the interior surface 34, 42 of the respective prosthetic cup 12 or cup insert 14 such that the surface area of the distal end surface 40, contacting the interior surface 34, 42 of the prosthetic cup 12 or insert 14, is minimized. At the opposite proximal end portion 36 of the upper body portion 32 of the primary cup contacting member 26, resides a proximal end surface 46 having a curved concave surface. As illustrated in FIGS. 2, 4, and 6-7, a slot 48, having an elongated slot length, extends through the thickness of both the lower body and upper body portions 30, 32 of the primary cup contacting member 26. In a preferred embodiment, the width of the distal end 38 of the upper body portion 32 is greater than the width of the proximal end 36 of the upper body portion 32.

As previously mentioned, the lower body portion 30 of the primary cup contacting member 26 extends below the upper body portion 32. The lower body portion 30 comprises opposing lower body portion sidewalls that form a lower body portion having a length, a width and a depth. In a preferred embodiment, a lip 50, as shown in FIG. 4, extends perpendicularly from the lower body portion sidewall. This lip 50, as will be explained in more detail, engages with the impaction plate 24 to provide a secure slidable relation therebetween.

As shown in FIGS. 2, 4, 6-7 and 9, the secondary cup contacting member 28 comprises a distal secondary member end portion 52 spaced from a proximal secondary member end portion 54. The secondary cup contacting member 28 further comprises a top sidewall 56 extending to a bottom sidewall 58 and a left sidewall 60 extending to a right sidewall 62 defining a secondary member body 64. A secondary body throughbore 66 extends perpendicularly with respect to imaginary axis B-B therethrough. As illustrated in FIGS. 2, 4, 6-7, and 9, the secondary cup contacting member 28 is positioned on the impaction plate 24 such that a secondary member proximal end surface 68 of the secondary member 28 faces towards the center of the impaction plate 24 and a distal end surface 70 of the secondary member 28 faces towards the outer perimeter of the secondary member 28.

As shown in FIGS. 2, and 6-7, the primary cup contacting member 26 and the secondary cup contacting member 28 are positioned such that their respective distal end surfaces 40, 70 form imaginary arcs of differing diameters. More specifically, the distal end surfaces 40 of the primary cup contacting members 26 are positioned about an outer perimeter of the impaction plate 24. The distal end surface 70 of the secondary cup contacting members 28 is preferably positioned nearer to the center of the impaction plate 24, and thus, forms an imaginary arc having a diameter that is smaller than the arc formed by the distal end surfaces 40 of the primary cup contacting members 26. This is designed such that when the prosthetic cup implant 12 is positioned on the end of the prosthesis engaging subassembly 20, the distal end surfaces 40, 70 of the respective primary and secondary cup contacting members 26, 28 contact the interior surfaces 34, 42 of the cup 12 and/or insert 14 at differing depths therewithin. More specifically, as illustrated in FIGS. 11, 13, and 15-16, the end surface 40 of the primary cup contacting members 26 is positioned within a cup groove 72 residing just within an outer perimeter 74 of the cup 12, while a front surface 76 of the distal end 38 of the primary cup contacting members 26 contacts a portion of a proximal end surface 78 of the cup insert 14. In addition, the distal end surface 70 of the secondary cup contacting members 28 contacts the interior surface 34 of the cup insert 14 distal of the cup groove 72 and deeper within the cup 12. Although the use of the cup insert 14 is preferred, the impactor 10 of the present invention may be used without the insert 14.

FIGS. 2, 4, 6-7, and 11, illustrate an embodiment of the impaction plate 24. With respect to the plate 24 mounted to the distal end of the impactor 10 housing 16 (FIG. 1), the plate 24 comprises a distal impaction plate surface 80 spaced from a proximal impaction plate surface 82, an impaction plate thickness 84 therebetween. The impaction plate further comprises an impaction plate opening 86 that extends through the thickness 84 of the plate 24. In a preferred embodiment, the opening 86 is dimensioned such that a web portion 88 (FIG. 2), extending from a distal end 90 of the housing 16, is positionable therewithin. The opening 86 is preferably positioned about the center of the plate 24 such that a central longitudinal axis C-C extends perpendicularly therethrough. In a preferred embodiment, the impaction plate 24 may have a diameter that is about equal to a base diameter of a prosthesis cup 12.

As shown in FIG. 4, a pair of secondary cup contacting alignment rails 92 extend outwardly from the distal surface 80 of the impaction plate 24. The rails 92 are preferably positioned in a parallel orientation to imaginary axis B-B. Each alignment rail 92 forms a "guide rail" on which one of the secondary cup contacting members 28 slide in a parallel orientation along axis B-B. Corresponding secondary cup contacting member grooves (not shown), positioned within a backside surface of each of the secondary cup contacting members 28, engage with the rails 92, thus securing the secondary cup contacting members 28 in a slidable relationship along the distal surface 80 of the impaction plate 24.

Furthermore, as illustrated in FIG. 4, a pair of secondary cup contacting pins 94 extend perpendicularly from the distal surface 80 of the impaction plate 24. The pins 94 are preferably positioned through the secondary cup contacting member throughbores 66 that extend through the thickness of the secondary cup contacting members 28. In a preferred embodiment, each throughbore 66 is an oblong opening that is slightly bigger than the diameter of the elongated body of the pin 94. This allows the secondary cup contacting pin 94 to secure the secondary member 28 to the plate 24 while providing a limited amount of travel of the member 28 on the distal surface 80 of the plate 24. In a preferred embodiment, the opening 66 that extends through the thickness of each of the secondary cup contacting members 28 may be designed similar to a slot, thereby providing increased length of travel of the members 28.

In addition, the impaction plate 24 may comprise a primary member channel 96 that resides within the thickness 84 of the impaction plate 24. More specifically, as illustrated in FIG. 4, the primary member channel 96 extends longitudinally along imaginary axis A-A, from the outer perimeter of the plate 24 to the central plate opening 86, within the thickness 84 of the plate 24. The channel 96 is designed with an overhang portion 98 that captures the corresponding lip portion 50 of the primary cup contacting members 26 therewithin. As shown in FIG. 4, the lip portion 50 extends about perpendicular from a backside body portion 100 of each of the primary cup contacting members 26. When inserted in the channel 96, the primary cup contact member 26 is in a slideable relationship therewithin.

As shown in FIG. 4, a pair of primary posts 102 extend upwardly from the distal surface of the channel 96. The long axes of the primary posts 102 are positioned about perpendicular to the distal impaction plate surface 80. A pair of primary bias members 104, having an elongated length with respective first and second ends, 105, 107 are preferably positioned adjacent to the primary posts 102. More specifically, the primary bias members 104 are positioned lengthwise along axis A-A, within the primary member channel 96, such that their first ends 105 are in a contactable relationship with the primary post 102. The second ends 107 of the primary bias members 104 extend towards the outer perimeter of the impaction plate 24. In a preferred embodiment, the primary bias members 104 and the primary posts 102 are positioned within the slots 48 of the respective primary cup contacting members 26. As shown in FIGS. 10, 13, and 15-16, the primary bias members 104 exert an outward force against the primary posts 102 such that the distal end portions 38 of the primary cup contacting members 26 extend outwardly from the central opening of the impaction plate 24. More specifically, as shown in FIGS. 10, 13, and 15-16, the primary bias members 104 exert a force on the primary posts 102 such that the distal end portions 38 of the primary members 26 extend past or out beyond the outer perimeter of the impaction plate 24.

As shown in FIG. 4, the impaction plate 24 may comprise a series of impaction plate nodules 106. These nodules 106 extend outwardly from the distal surface 80 of the impaction plate 24. The nodules 106 are designed such that they align with a corresponding cup recess 108 that is positioned about the outer perimeter 74 of the cup 12 as illustrated in FIG. 3. In a preferred embodiment, when the prosthesis cup 12 is positioned at the end of the prosthesis cup attachment assembly 20, the nodules 106 reside within the respective cup recesses 108 (FIG. 3). This interaction between the nodules 106 and cup recesses 108 therefore provides additional stability during the cup impaction process. The nodules 106 may be constructed having a multitude of non-limiting shapes and forms. As shown in FIGS. 2 and 4, each of the nodules 106 have a "half-moon" shape, however they may also be of a curved, round, rectangular, triangular, or hexagonal form. In any case, the nodules 106 are designed to fit within the respective cup recess 108.

An embodiment of the wedging assembly 33 is shown in FIGS. 1-2, 5-11, 13, 15 and 16. As shown, the wedging assembly 33 comprises a wedging assembly proximal end portion 109 (FIG. 6) spaced from a wedging assembly distal end portion 111 that extends longitudinally along imaginary axis C-C (FIG. 1). In a preferred embodiment, the proximal end portion 109 of the wedging assembly 33 is positioned about the opening 86 of the distal surface 80 of the impaction plate 24. The wedging assembly proximal end portion 109 may comprise a helical grooved portion 110 therewithin that secures to a threaded portion 112 of the distal end of a drive rod 114 of the drive train 18, as illustrated in FIGS. 1, 1A, 6 and 7.

Figure 5:
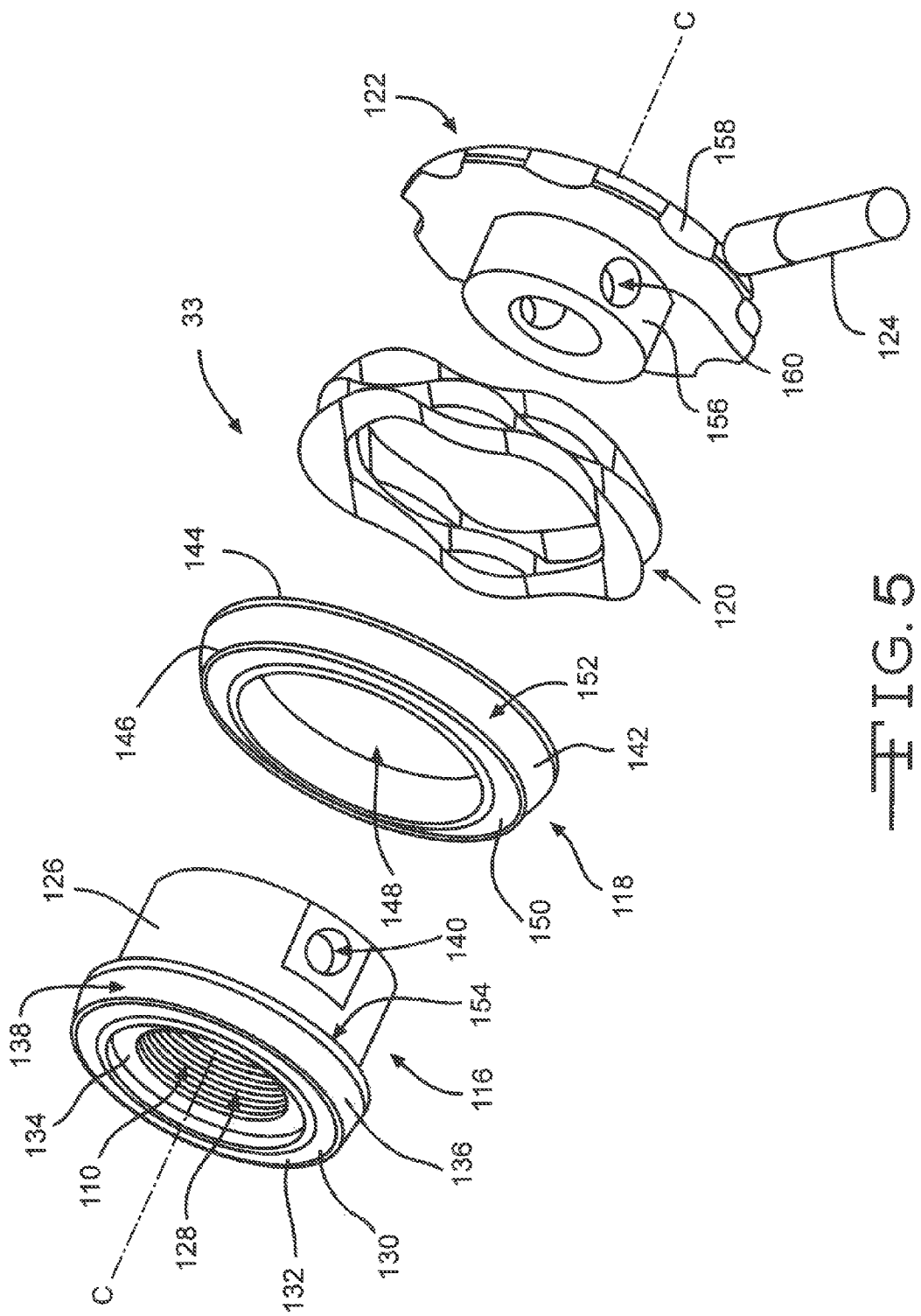
FIG. 5 shows a magnified perspective view of the components comprising an embodiment of the wedging assembly.

As shown in FIG. 5, the wedging assembly 33 comprises a first body 116, a second conical body 118, a cylindrical wave-shaped bias member 120, an end cap 122 and a locking pin 124. The first body 116 has annular sidewall 126 that extends from a ramp surface 138 at its distal end to a first proximal end, a first throughbore 128 extends longitudinally therethrough.

In a preferred embodiment, an annular gasket 130 circumferentially extends around the proximal end of the first body 116. As shown, the gasket 130 protrudes outwardly from the outer perimeter of the annular sidewall 126. As shown, in FIG. 5, the gasket 130 has a gasket end sidewall 132 that is positioned about perpendicular to the longitudinal axis of the annular sidewall 126 of the first body 116. The gasket end sidewall 132 encircles the throughbore 128 of the first body 116. Furthermore, an annular recess 134 is provided radially inwardly of the gasket 130 at the proximal end of the first body 116. The gasket recess 134 is provided to further engage the web portion 88 (FIG. 2) of the housing 16.

A first cone band 136 extends circumferentially around the proximal end of the first body 116. As shown, the first cone band 136 forms an exterior sidewall surrounding the gasket 130 and having a band frustro-conical shape that extends from the proximal end of the body 116 to a point distal of the cone's proximal end. In a preferred embodiment, the first cone band 136 may have an angled or ramped orientation with respect to the annular sidewall 126 of the first body 116. In an embodiment, the first band 136 may be positioned in an angled relationship ranging from about 5° to about 50° with respect to the exterior surface of the annular sidewall 126. As shown in FIG. 5, the first cone band 136 is positioned such that the diameter, at the proximal end of the first body 116, is smaller than the diameter located at the distal end of the first body 116.

In a preferred embodiment, as illustrated in FIGS. 13-16, the first cone band 136 forms a ramp surface 138 that pushes against the proximal end surface 46 of the primary cup contacting member 26. The ramped surface 138 of the first cone band 136, wedges against the proximal end surface 46 of the primary cup contacting member 26, thereby preventing movement and locking the primary cup contacting member 26 in place against the interior surface of the cup 12. More specifically, as shown in FIGS. 11, 13, 15 and 16, the ramped surface 138 of the first cone band 136 wedges against the proximal end surface 46 of the primary cup contacting member 26 which thrusts the distal end surface 40 of the primary cup contacting member 26 against the interior surfaces 34, 42 of the cup 12 and/or insert 14. In addition, a second first cone throughbore 140 extends perpendicularly through the annular sidewall 126 of the first conical body 116 at the distal end thereof.

The second conical body 118 resides distal of the first conical body 116. The second conical body 118 is of a general cone shape having an annular second conical body sidewall 142 extending from a second conical body distal end 144 to a second conical body proximal end 146. A second conical body throughbore 148 extends longitudinally therethrough. A second cone end sidewall 150 resides at the proximal end of the secondary conical body 118. In a preferred embodiment, the end sidewall 150 extends circumferentially around the throughbore opening 148 in a perpendicular relationship therewith. The second conical body sidewall 142 has a frusto-conical shape such that the diameter of the distal end 144 of the secondary conical body 118 is greater than the diameter at the proximal end 146 of the secondary conical body 118. In an embodiment, the annular second conical body sidewall 142 may be positioned at an angled relationship ranging from about 5° to about 50° with respect to longitudinal axis C-C as shown in FIG. 5. This angled orientation of the conical body sidewall 142 forms a second cone ramp surface 152.

In a preferred embodiment, the wedging assembly 33 is constructed such that the annular sidewall 126 of the first conical body 116 is positioned through the throughbore 148 of the second conical body 118. In a preferred embodiment, a ledge 154 of the gasket portion 130 of the first body 116 is positioned on an exterior surface of the end sidewall portion 150 of the second conical body 118. The wedging assembly 33 is constructed such that the diameter at the distal end 111 of the assembly 33 is greater than the diameter at the proximal end 109 of the assembly 33 (FIG. 2). Specifically, as shown in FIGS. 2, and 5-16, the wedging assembly 33 is constructed such that the diameter of the second conical body 118 is greater than the diameter of the first body 116 within the assembly 33. Thus, the wedging assembly 33 has a ramped surface of increasing diameter from the proximal end portion 109 of the wedging assembly 33 to the distal end portion 111 thereof.

The annular wave-shaped bias member 120 is preferably positioned between the second conical body 118 and the end cap 122 of the wedging assembly 33. The bias member 120 provides a bias force against the first and second conical bodies 116, 118. As shown, the end cap 122 comprises a cylindrical sidewall 156 that extends from a proximal end to an enlarged gripping portion 158. An end cap throughbore 160 resides perpendicularly through the annular sidewall 156. The throughbore 160 is dimensioned such that the locking pin 124 may be positioned therethrough. The locking pin 124 received in throughbores 140 and 160 connects the end cap 122 to the first body 116 with the second conical body 118 and the bias member 120 positioned therebetween.

In operation, a prosthetic cup implant 12 is initially positioned at the distal end of the prosthesis engaging subassembly 20. As shown in FIGS. 11, 13, 15, and 16, a portion of the distal end 38 of the primary cup contacting body 26 is positioned within the groove 72 (FIG. 13) residing within the proximal end 74 of the prosthesis cup 12. Specifically, the prosthesis cup 12 is positioned such that the distal end surface 40 of the primary cup contacting body 26 contacts within an interior surface 161 of the groove 72 (FIG. 15) of the cup 12. The primary bias members 104, positioned within the slots 48 of the primary cup contacting members 26, exert a force against the primary posts 102 which biases the distal ends 38 of the members 26A, 26B to extend forward past the outer perimeter of the impaction plate 24.

A prosthesis cup 12 is positioned over the distal end portion 38 of the primary cup contacting members 26A, 26B. Specifically, a prosthetic cup 12 is positioned over the distal end portion 38 of the primary cup contacting members 26A, 26B such that a distal end surface 40 or ridge 44 of the members 26A, 26B resides within the groove 72 of the cup 12. In addition, a portion of a front surface 76 of the distal end portion 38 of the primary cup contacting members 26A, 26B contacts a proximal end surface 78 of the prosthetic cup insert 14.

Once the prosthetic cup implant 12 is initially positioned at the distal end of the prosthesis engaging subassembly 20, the wedging assembly 33 is utilized to lock the prosthesis cup 12 in position. Specifically, a downward movement of a lever 164 of the drive train 18 (FIG. 1) towards an exterior surface 166 of the housing 16 at the proximal end of the impactor 10 initiates movement of the drive train and the wedging assembly 33 of the prosthesis engaging subassembly 20 in a proximal direction. Continued downward movement of the lever 164 towards the exterior surface 166 of the housing 16, thereby pulls the wedging assembly 33 in a further proximal direction within the prosthesis engaging subassembly 20. As the wedging assembly 33 moves proximally, the combination of the ramping surfaces 138, 152 of the first conical band 136 and the second conical body sidewall 142, wedges against the respective proximal end surfaces 46, 68 of the primary and secondary members 26, 28. As shown in FIGS. 11-14, as the first conical band 136 is moved in a proximal direction by the drive train 18, the exterior surface 138 of the first conical band 136 contacts the proximal end surfaces 46 of the primary cup contacting members 26, thus preventing the distal ends 40 of the primary cup contacting members 26A, 26B from moving in an inwardly direction away from the groove 72 of the cup 12 and towards the central opening 86 of the impaction plate 24. In other words, movement of the drive train 18 forces the primary cup contacting members 26A, 26B outwardly into engagement with the prosthesis cup 12.

Proximal movement of the second cone sidewall 142 causes the distal end surface 70 of the secondary cup contacting members 28A, 28B into contact with the interior surface 34 of the cup 12, particularly an interior surface 42 of the insert 14 positioned within the cup 12. As shown in FIGS. 11-16, the exterior surface 152 of the second frusto-conical band 142 contacts the proximal end surface 68 of the secondary cup contacting members 28A, 28B thereby exerting an outward force therebetween. In other words, the exterior ramp surface 152 of the second band 142 of the second conical body 118 wedges against the proximal end surfaces 68 of the secondary cup contacting members 28A, 28B causing the distal end surfaces 70 of the secondary members 28A, 28B to contact the end surface 78 of the insert 14. In this manner, movement of the secondary cup contacting members 28A, 28B locks the insert 14 in place.

Figure 12:
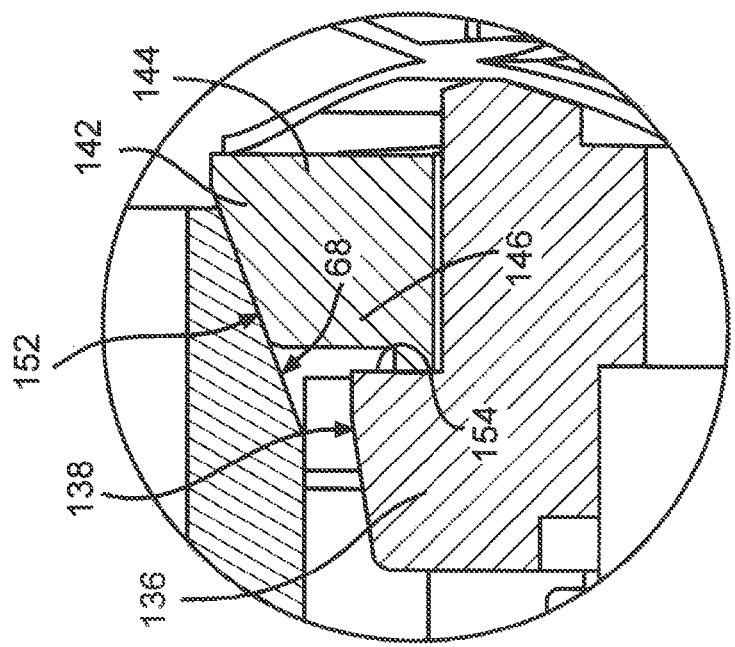
FIG. 12 illustrates a magnified cross-sectional view of an embodiment of the position of the first and second bands of the first and second conical bodies with respect to the proximal end surfaces of the primary and secondary cup contacting members shown in FIG. 11.
Figure 11:
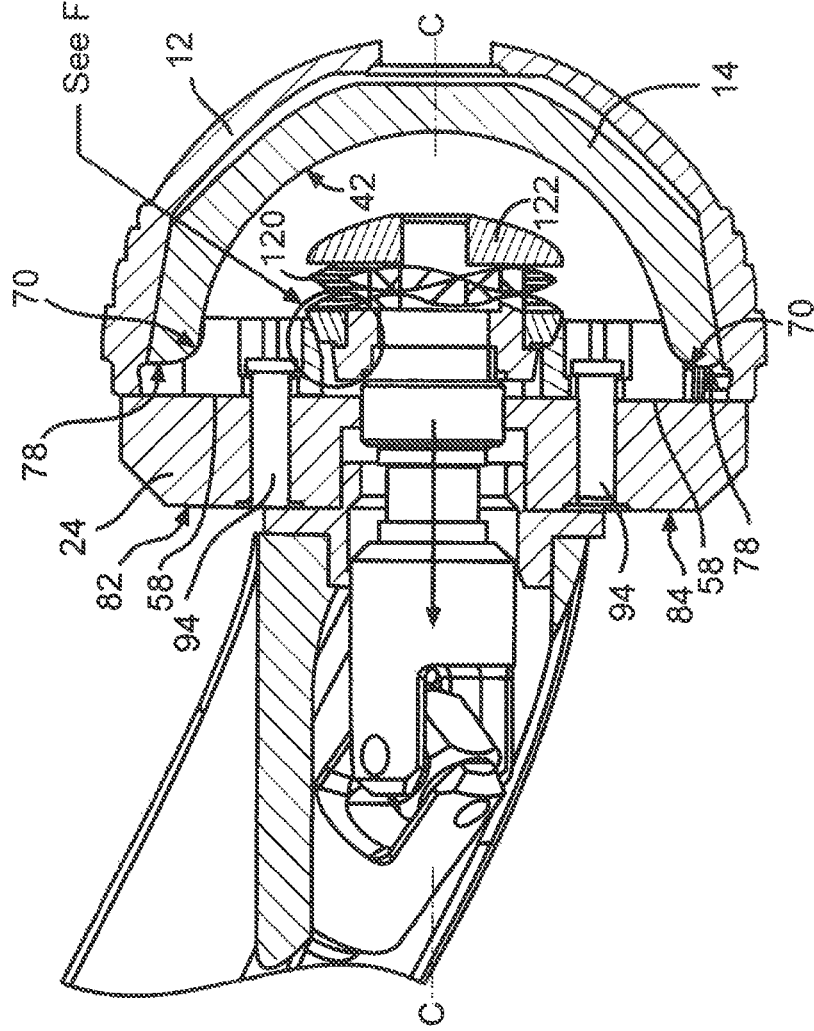
FIG. 11 shows a cross-sectional view of an embodiment of a prosthesis cup being connected to the prosthesis engaging subassembly, the wedging assembly initially moving in a proximal direction.

In a preferred embodiment, when the lever 164 is moved in a downward direction towards the exterior surface 166 of the housing 16, the wedging assembly 33 begins to move in a proximal direction towards the central opening 86 of the impaction plate 24. Continued proximal movement of the wedging assembly 33 causes the second band 142 of the second cone 118 to first come into contact with the proximal end surfaces 68 of the second cup contacting members 28A, 28B. As shown in FIGS. 11 and 12, as the wedging assembly 33 is further moved in a proximal direction, the distal end surfaces 70 of the secondary cup contacting members 28A, 28B move outwardly and contact at least a portion of the interior surface of the cup insert 14, particularly a portion of the proximal end surface 78 of the insert 14. As the secondary cup contacting members 28A, 283 slide along the distal surface 80 of the impaction plate 24, alignment rails 92, positioned within the secondary cup contacting member grooves (not shown), ensure the secondary members 28A, 28B move about parallel to axis B-B.

As shown in FIGS. 13 and 14, as the wedging assembly 33 is moved even further in a proximal direction, the first conical band 136 of the first body 116 contacts the proximal end surfaces 46 of the primary cup contacting members 26A, 26B to force them in an outwardly direction. Therefore, the distal end portion 32 of the primary cup contacting members 26A, 26B are prevented from retracting towards the central opening 86 of the impaction plate 24. In addition, the distal surfaces 40 of the primary cup contacting members 26A, 26B are trapped or locked within the groove 72 of the cup 12. It is noted that as the primary cup contacting members 26A, 26B slide along the distal surface 80 of the impaction plate 24, the primary posts 94 which extend through the slot 48 of the primary members 26A, 265, ensure primary members 26A, 26B move about parallel to axis A-A.

When the lever 164 reaches its full downward position and the wedging assembly 33 is positioned in its full proximal position, as shown in FIGS. 15 and 16, the distal, surfaces 70 of the secondary cup contacting members 28A, 285 are in a contactable relationship with the interior surface of the cup insert 14, and the distal surfaces 40 of the primary cup contacting members 26A, 26B, are in a contactable relationship with the interior surface of the cup groove 72 and the end surface 78 of the cup insert 14. In other words, primary cup contacting members 26A, 26B are forced into contact with the cup 12 by surface 138 and secondary cup contacting members 28A, 285 are forced into contact with the insert 14 by surface 152.

The second cone 118 is biased against the bias member 120 such that impaction forces applied to the cup insert 14 by the secondary cone members 28A, 28B are primarily absorbed by the bias member 120. Thus, when an impaction force is applied to the end of the handle 22, the magnitude of the force is primarily absorbed by the bias member 120. In addition, some of the impaction force is absorbed by the first bias members 104 before that force is transferred to the primary cup contacting member 26. Furthermore, the use of the respective distal end surfaces 40 and 70, with a minimum amount of surface area, reduces the magnitude of the impaction force transmitted to the cup 12 or insert 14. This helps prevent damage to the cup 12 and insert 14 during their installation into an acetabulum.

In a preferred embodiment, the prosthesis engaging subassembly 20 is connected to the distal end 90 of the housing 16. The cylindrical drive rod 114, which is connected to a cylindrical piston 168, slides through the central axial bore 86 that penetrates through the impaction plate 24. The cylindrical drive rod 114 is preferably threaded. The cylindrical rod 114 is threaded into a corresponding threaded groove of the axial through-bore 128 of the primary body 116 of the wedging assembly 33 securing it in place as shown in FIGS. 6-10.

In a preferred embodiment, the impaction plate 24 may be made of a metallic material such as stainless steel, MP35N, aluminum or the like. The primary and secondary cup contacting members 26A, 26B, 28A, 28B are preferably made of a polymeric material such as, but not limited to synthetic rubber, neoprene, nylon, poly vinyl chloride (PVC), polystyrene, polyethylene, polypropylene, polyacrylonitrile, polyvinyl butyral (PVB), silicone, polyether ether ketone (PEEK), and the like.

With respect to the drive train 18, the piston 168 is connected by way of a first U-joint 170 to a lever 172 which slides in a pivoting sleeve 174 fixed to the housing 16 via a pivot 176. The lever 172 is connected via a second. U-joint 178 to a second pivoting lever 180 which is fixed to pivot in a catch 182 (FIG. 1) on a pivot pin 184. The catch 182 is essentially a divot or a seat cut into the housing 16, against which the pivot pin 184 of the lever 180 is captured when a slide is slid over the pin 184 when engaged against the seat.

A slideable sleeve 186 slides over the lever 180 and has a trunnion 188 to which a rod 190 is pivotally attached. The rod 190 passes through a one-way catch 192 in the housing 16. The one-way catch 192 can be a captured split wedge sleeve 194 having an inner diameter that just matches the outer diameter of the rod 190. The split wedge sleeve 194 is captured in a recess having a matching conical surface that surrounds the sleeve so as to allow the rod 190 to slide into the housing 16, but to prevent the rod 190 from sliding out of the housing 16 unless an unlock lever (not show) is activated. Manipulation of the lever lifts the sleeve 186 out of engagement with the conical surface into an unlocked position to permit the rod 190 to back out of the housing 16. Any number of alternative one-way lock devices may be used, however, the selection of which being within the skill of a person of ordinary skill in this field. For greater detail regarding the drive train 18 supported by the housing 16, reference is made to U.S. Pat. No. 7,682,363 to Burgi et al., which is assigned to the assignee of the present invention and incorporated herein by reference.

Once correctly positioned within the body, impaction forces are delivered to the proximal end of the impactor 10. These impaction forces are intended to drive the prosthetic cup implant 12 to the desired location within the body. Once the cup implant 12 is securely in place, the tension between distal end surfaces 40, 70 of the members 26A, 26B and 28A, 28B against the respective primary and secondary cup contacting members 26A, 26B, 28A and 28B are released. A release button not shown) for the one-way catch 192 is depressed allowing the rod 190 to move in a reverse direction, thereby relieving the applied pressure of the distal end surfaces 40, 70 to the prosthetic cup 12 and/or insert 14. The operator may then pulls back on the handle 22 thereby retracting the impaction plate 24 and wedging assembly 33 of the prosthesis engaging subassembly 20 from the body. The inserter 10 is removed from the body leaving the double mobility prosthetic cup 12 behind within the body.

The inserter 10 is designed to be disassembled for cleaning by simply sliding the slide back so as to release the pivot. 182 and then lifting the drive train 18 out of the housing, but allowing the drive train to remain pivotally connected at pivot 176. As the drive train 18 is pivoted, the piston 168 is drawn out of the housing cavity. To reassemble after cleaning, the piston 168 is reinserted into the housing cavity and the drive train 18 is rotated back into position, with the one way locking mechanism entering its receiver and the pivot 176 again entering into the catch 182. The slide is then slid over the pivot 176 and the inserter 10 is again ready for use.

The present invention can be packaged in a kit offering a variety of double mobility prosthetic implants 12 of different sizes and diameters. The inserter 10 and assorted double mobility implants 12 and subassemblies 20 can be packaged in a case with recesses which conveniently hold the components in a convenient, easy to access manner.

The attached drawings represent, by way of example, different embodiments of the subject of the invention. Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An impactor for aiding a surgeon in controlling the installation of a prosthesis cup, the impactor comprising:
    a) an impaction plate, comprising:
        i) a proximal plate surface spaced from a distal plate surface by a perimeter edge providing a plate thickness;
        ii) a plate opening extending along a longitudinal axis through the plate thickness and to the proximal and distal plate surfaces; and
        iii) first and second spaced apart posts extending from the impaction plate substantially parallel to the longitudinal axis;
    b) at least a first and a second primary cup contact members, each primary contact member comprising:
        i) a proximal primary contact surface spaced from a distal primary contact surface;
        ii) first and second primary elongate slots provided in the respective first and second contact members, each slot comprising opposed proximal and distal slot ends spaced from the respective proximal and distal primary contact surfaces,
        iii) wherein the first and second primary contact members are positioned in opposition to each other in a slidable relationship along the distal surface of the impaction plate with their respective proximal contact surfaces facing the impaction plate opening and with their slots received on the respective first and second posts extending from the impaction plate so that respective primary slot longitudinal axes intersect the first and second posts and the respective opposed slot ends;
    c) at least a first and a second primary biasing members residing in the respective elongate slots of the first and second primary contact members, wherein each primary biasing member biases from the respective first and second posts extending from the impaction plate to a distal end of the respective elongate slots to thereby bias the distal surfaces of the first and second primary contact members beyond the perimeter plate edge;
    d) a wedging assembly comprising at least a first body having a first inclined surface extending proximally and inwardly toward the longitudinal axis;
    e) an impactor housing comprising a proximal housing end and a distal housing end;
    f) a drive train at least partially housed inside the impactor housing, the drive train comprising a proximal drive train portion spaced from a distal drive train portion having a distal drive train end, wherein the proximal drive train portion is located adjacent to the proximal housing end and the distal drive train portion is located adjacent to the distal housing end with the distal drive train end received in the opening in the impaction plate and being detachably connected to the wedging assembly; and
    g) wherein a handle at the proximal housing end is manipulatable to move the impaction plate adjacent to a prosthesis cup with the distal contact surfaces of the primary contact members biased into engagement with a mating surface of the prosthesis cup, and
    h) wherein subsequent actuation of the proximal drive train portion from a first position spaced from the impactor housing to a second position spaced closer to the housing than the first spaced position draws the first inclined surface of the first member of the wedging assembly in a proximal direction and into contact with first and second interior surfaces of the prosthesis cup to thereby lock the impaction plate to the prosthesis cup.

2. The impactor of claim 1 wherein the first inclined surface comprises a first frusto-conical shaped surface extending circumferentially around the first body.

3. The impactor of claim 2 wherein the first frusto-conical shaped surface extends proximally and inwardly toward the longitudinal axis at an angle ranging from 5° to 50°.

4. The impactor of claim 1 wherein the first and second primary cup contacting members reside within respective channels of the impaction plate, each channel extending along a respective primary slot longitudinal axis from adjacent to the plate opening to the perimeter edge.

5. The impactor of claim 1 wherein the distal contact surfaces of the first and second primary cup contacting members are contactable with a groove on an interior surface of the prosthesis cup.

6. The impactor of claim 1 wherein the wedging assembly further comprises an end cap distal the first body and wherein a third bias member is positioned between the first body and the end cap.

7. The impactor of claim 1 wherein the drive train further comprises:
   a) a first lever comprising a first lever proximal end spaced apart from a first lever distal end located adjacent to the distal housing end;
   b) a second lever comprising a second lever proximal end located adjacent to the proximal housing end and spaced apart from a second lever distal end;
   c) a drive rod comprising a drive rod proximal end spaced from a drive rod distal end, wherein the second lever distal end is in a universal joint relationship with the first lever proximal end, and wherein the first lever distal end is in a universal joint relationship with the drive rod proximal end and the drive rod distal end extends through the longitudinally extending opening of the impaction plate where the drive rod distal end is detachably connectable to the wedging assembly; and
   d) a first sleeve pivotably connected to the housing, wherein the first lever is in a slidable relationship with a first opening in the first sleeve disposed at an intermediate location between the first lever proximal end and the first lever distal end,
   e) wherein the second lever is pivotably supported by the housing, and
   f) wherein the second lever proximal end is manipulable from the first position to the second position spaced closer to the housing than the first position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the drive rod detachably connected to the wedging assembly to move along the longitudinal opening in the impaction plate with the drive rod distal end moving the wedging assembly from a first wedging assembly position spaced from the impaction plate to a second wedging assembly position closer to the impaction plate than the first wedging assembly position as the impaction plate is locked to the prosthesis cup.

8. The impactor of claim 1 wherein the housing is C-shaped.

9. The impactor of claim 1 wherein with an insert cup received inside a prosthesis cup, a first diameter of the impaction plate is larger than a maximum second diameter of the insert cup, but less than a maximum third diameter of the prosthesis cup.

10. A surgical kit, which comprises:
    a) at least one impactor according to claim 1;
    b) at least one prosthesis cup; and
    c) a case for organizing the components of the kit.

11. The impactor of claim 1 wherein the primary slot longitudinal axes are aligned substantially perpendicular to the longitudinal axis.

12. The impactor of claim 1 wherein the first and second posts extend distally from the distal surface of the impaction plate.

13. The impactor of claim 1 wherein with the impaction plate locked to the prosthesis cup, a proximal rim of the cup contacts the distal plate surface.

14. The impactor of claim 1 wherein:
    a) the impaction plate further comprises third and fourth spaced apart posts extending from the impaction plate substantially parallel to the longitudinal axis;
    b) at least a third and a fourth secondary cup contact members, each secondary contact member comprising
       i) a proximal secondary contact surface spaced from a distal secondary contact surface;
       ii) third and fourth secondary elongate slots provided in the respective third and fourth contact members, each slot comprising opposed proximal and distal slot ends spaced from the respective proximal and distal secondary contact surfaces,
       iii) wherein the third and fourth secondary contact members are positioned in opposition to each other in a slidable relationship along the distal surface of the impaction plate with their respective proximal contact surfaces facing the impaction plate opening and with their slots received on the respective third and fourth posts extending from the impaction plate so that respective secondary slot longitudinal axes intersect the third and fourth posts and the respective opposed slot ends; and
    c) the wedging assembly further comprising a second body having a second inclined surface extending proximally and inwardly toward the longitudinal axis;
    d) wherein with the impaction plate adjacent to a prosthesis cup, actuation of the proximal drive train portion from the first position to the second position to draw the inclined surface of the first member of the wedging assembly in the proximal direction and into contact with the proximal surfaces of the first and second primary contact members simultaneously draws the second inclined surface of the second member of the wedging assembly in the proximal direction and into contact with the proximal surfaces of the third and fourth secondary contact members to thereby lock the third and fourth secondary contact members supported by the impaction plate to the prosthesis.

15. The impactor of claim 14 wherein the second inclined surface comprises a second frusto-conical shaped surface extending circumferentially around the second conical body.

16. The impactor of claim 15 wherein the second frusto-conical shaped surface extends proximally and inwardly toward the longitudinal axis at an angle ranging from 5° to 50°.

17. The impactor of claim 14 wherein the primary slot longitudinal axes are substantially perpendicular to the secondary slot longitudinal, axes.

18. A surgical kit, which comprises:
a) at least one impactor according to claim 1;
b) at least one prosthesis cup assembly comprising an insert cup received inside a prosthesis cup; and
c) a case for organizing the components of the kit.

19. An impactor for aiding a surgeon in controlling the installation of a prosthesis cup, the impactor comprising:
a) an impaction plate, comprising:
i) a proximal plate surface spaced from a distal plate surface by a perimeter edge providing a plate thickness;
ii) a plate opening extending along a longitudinal axis through the plate thickness and to the proximal and distal plate surfaces; and
iii) first, second, third and fourth spaced apart posts extending from the impaction plate substantially parallel to the longitudinal axis;
b) at least a first and a second primary cup contact members, each primary contact member comprising:
i) a proximal primary contact surface spaced from a distal primary contact surface;
ii) first and second primary elongate slots provided in the respective first and second contact members, each slot comprising opposed proximal and distal slot ends spaced from the respective proximal and distal primary contact surfaces,
iii) wherein the first and second primary contact members are positioned in opposition to each other in a slidable relationship along the distal surface of the impaction plate with their respective proximal contact surfaces facing the impaction plate opening and with their slots received on the respective first and second posts extending from the impaction plate so that respective primary slot longitudinal axes intersect the first and second posts and the respective opposed slot ends;
c) at least a first and a second primary biasing members residing in the respective elongate slot of the first and second primary contact members, wherein each primary biasing member biases from the respective first and second post extending from the impaction plate to a distal end of the respective elongate slot to thereby bias the distal surface of the first and second primary contact member beyond the perimeter plate edge;
d) at least a third and a fourth secondary cup contact members, each secondary contact member comprising:
i) a proximal secondary contact surface spaced from a distal secondary contact surface;
ii) third and fourth secondary elongate slots provided in the respective third and fourth contact members, each slot comprising opposed proximal and distal slot ends spaced from the respective proximal and distal secondary contact surfaces,
iii) wherein the third and fourth secondary contact members are positioned in opposition to each other in a slidable relationship along the distal surface of the impaction plate with their respective proximal contact surfaces facing the impaction plate opening and with their slots received on the respective third and fourth posts extending from the impaction plate so that respective secondary slot longitudinal axes intersect the third and fourth posts and the respective opposed slot ends; and
e) a wedging assembly, comprising:
i) at least a first body having a first inclined surface extending proximally and inwardly toward the longitudinal axis;
ii) a second body having a second inclined surface extending proximally and inwardly toward the longitudinal axis;
iii) an end cap supported by the second body; and
iv) a wave-shaped third bias member positioned between the second body and the end cap;
f) an impactor housing comprising a proximal housing end and a distal housing end;
g) a drive train at least partially housed inside the impactor housing, the drive train comprising a proximal drive train portion spaced from a distal drive train portion having a distal drive train end, wherein the proximal drive train portion is located adjacent to the proximal housing end and the distal drive train portion is located adjacent to the distal housing end with the distal drive train end received in the opening in the impaction plate and being detachably connected to the wedging assembly; and
h) wherein a handle at the proximal housing end is manipulatable to move the impaction plate adjacent to a prosthesis cup with the distal contact surfaces of the primary contact members biased into engagement with a mating surface of the prosthesis cup, and
i) wherein subsequent actuation of the proximal drive train portion from a first position spaced from the impactor housing to a second position spaced closer to the housing than the first spaced position draws the first inclined surfaces of the first member of the wedging assembly in a proximal direction and into contact with first and second interior surfaces of the prosthesis cup and simultaneously draws the second inclined surface of the second member of the wedging assembly in the proximal direction and into contact with the proximal surfaces of the third and fourth secondary contact members to thereby lock the first and second primary contact members and the third and fourth secondary contact members to the prosthesis to thereby lock the impaction plate to the prosthesis cup.

20. The impactor of claim 19 wherein the first inclined surface comprises a first frusto-conical shaped surface extending circumferentially around the first body and wherein the first frusto-conical shaped surface extends proximally and inwardly toward the longitudinal axis at an angle ranging from 5° to 50°.

21. The impactor of claim 19 wherein with the impaction plate locked to the prosthesis cup, a proximal rim of the cup contacts the distal plate surface.

22. The impactor of claim 19 wherein the first and second primary cup contacting members reside within respective channels of the impaction plate, each channel extending along a respective primary slot longitudinal axis from adjacent to the plate opening to the perimeter edge.

23. The impactor of claim 19 wherein the second inclined surface comprises a second frusto-conical shaped surface extending circumferentially around the second conical body and wherein the second frusto-conical shaped surface extends proximally and inwardly toward the longitudinal axis at an angle ranging from 5° to 50°.

24. The impactor of claim 19 wherein the distal contact surfaces of the first and second primary cup contacting members are contactable with a groove on an interior surface of the prosthesis cup.

25. The impactor of claim 19 wherein the drive train further comprises:
a) a first lever comprising a first lever proximal end spaced apart from a first lever distal end located adjacent to the distal housing end;

b) a second lever comprising a second lever proximal end located adjacent to the proximal housing end and spaced apart from a second lever distal end;

c) a drive rod comprising a drive rod proximal end spaced from a drive rod distal end, wherein the second lever distal end is in a universal joint relationship with the first lever proximal end, and wherein the first lever distal end is in a universal joint relationship with the drive rod proximal end and the drive rod distal end extends through the longitudinally extending opening of the impaction plate where the drive rod distal end is detachably connectable to the wedging assembly; and d) a first sleeve pivotably connected to the housing, wherein the first lever is in a slidable relationship with a first opening in, the first sleeve disposed at an intermediate location between the first lever proximal end and the first lever distal end, e) wherein the second lever is pivotably supported by the housing, and f) wherein the second lever proximal end is manipulable from the first position to the second position spaced closer to the housing than the first position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the drive rod detachably connected to the wedging assembly to move along the longitudinal opening in the impaction plate with the drive rod distal end moving the wedging assembly from a first wedging assembly position spaced from the impaction plate to a second wedging assembly position closer to the impaction plate than the first wedging assembly position as the impaction plate is locked to the prosthesis cup.

26. The impactor of claim 19 wherein the housing is C-shaped.

27. The impactor of claim 19 wherein with an insert cup received inside a prosthesis cup, a first diameter of the impaction plate is larger than a maximum second diameter of the insert cup, but less than a maximum third diameter of the prosthesis cup.

28. A surgical kit, which comprises:
a) at least one impactor according to claim 19;
b) at least one prosthesis cup; and
c) a case for organizing the components of the kit.

29. A surgical kit, which comprises:
a) at least one impactor according to claim 19;
b) at least one prosthesis cup assembly comprising an insert cup received inside a prosthesis cup; and
c) a case for organizing the components of the kit.

30. The impactor of claim 19 wherein the primary slot longitudinal axes are aligned substantially perpendicular to the longitudinal axis.

31. The impactor of claim 19 wherein the first and second posts extend distally from the distal surface of the impaction plate.

32. The impactor of claim 19 wherein, with the impaction plate locked to the prosthesis cup, a proximal rim of the cup contacts the distal plate surface.

33. The impactor of claim 19 wherein the primary slot longitudinal axes are substantially perpendicular to the secondary slot longitudinal axes.

34. An impactor for aiding a surgeon in controlling the installation of a prosthesis cup, the impactor comprising:
a) an impaction plate, comprising:
i) a proximal plate surface spaced from a distal plate surface by a perimeter edge providing a plate thickness;
ii) a plate opening extending along a longitudinal axis through the plate thickness and to the proximal and distal plate surfaces; and
iii) first and second spaced apart posts extending from the impaction plate substantially parallel to the longitudinal axis;

b) at least a first and a second primary cup contact members, each primary contact member comprising:
1) a proximal primary contact surface spaced from a distal primary contact surface;
ii) first and second primary elongate slots provided in the respective first and second contact members, each slot comprising opposed proximal and distal slot ends spaced from the respective proximal and distal primary contact surfaces,
iii) wherein the first and second primary contact members are positioned in opposition to each other in a slidable relationship along the distal surface of the impaction plate with their respective proximal contact surfaces facing the impaction plate opening and with their slots received on the respective first and second posts extending from the impaction plate so that respective primary slot longitudinal axes intersect the first and second posts and the respective opposed slot ends;

c) at least a first and a second primary biasing members residing in the respective elongate slots of the first and second primary contact members, wherein each primary biasing member biases from the respective first and second post extending from the impaction plate to a distal end of the respective elongate slot to thereby bias the distal surface of the first and second primary contact member away from the plate opening;

d) a wedging assembly comprising at least a first body having a first inclined surface extending proximally and inwardly toward the longitudinal axis;

e) an impactor housing comprising a proximal housing end and a distal housing end;

f) a drive train at least partially housed inside the impactor housing, the drive train comprising a proximal drive train portion spaced from a distal drive train portion having a distal drive train end, wherein the proximal drive train portion is located adjacent to the proximal housing end and the distal drive train portion is located adjacent to the distal housing end with the distal drive train end received in the opening in the impaction plate and being detachably connected to the wedging assembly; and g) wherein a handle at the proximal housing end is manipulatable to move the impaction plate adjacent to a prosthesis cup, and h) wherein subsequent actuation of the proximal drive train portion from a first position spaced from the impactor housing to a second position spaced closer to the housing than the first spaced position, draws the first inclined surface of the first member of the wedging assembly in a proximal direction and into contact with first and second interior surfaces of the prosthesis cup to cause the distal contact surfaces of the primary contact members to contact a mating surface of the prosthesis cup and thereby lock the impaction plate to the prosthesis cup.

35. The impactor of claim 34 wherein the first inclined surface comprises a first frusto-conical shaped surface extending circumferentially around the first body.

36. The impactor of claim 34 wherein the first and second primary cup contacting members reside within respective channels of the impaction plate, each channel extending from adjacent to the plate opening to the perimeter edge.

37. The impactor of claim 34 wherein the housing is C-shaped.

38. The impactor of claim 34 wherein with the impaction plate locked to the prosthesis cup, a proximal rim of the cup contacts the distal plate surface.

* * * * *

UNITED STATES PATENT AND TRADEMARK OFFICE
CERTIFICATE OF CORRECTION

| | | |
|---|---|---|
| PATENT NO. | : 9,028,502 B2 | Page 1 of 1 |
| APPLICATION NO. | : 13/625023 | |
| DATED | : May 12, 2015 | |
| INVENTOR(S) | : Jonas Burgi | |

It is certified that error appears in the above-identified patent and that said Letters Patent is hereby corrected as shown below:

In The Claims

Column 15, line 6 (Claim 19, line 1) after the word "controlling" delete the ","

Column 17, line 16 (Claim 25, line 20) after the word "in" delete the ","

Signed and Sealed this
Fifteenth Day of December, 2015

Michelle K. Lee
*Director of the United States Patent and Trademark Office*